United States Patent
Baek et al.

(10) Patent No.: US 11,492,330 B2
(45) Date of Patent: Nov. 8, 2022

(54) ORGANIC COMPOUND, AND ORGANIC LIGHT-EMITTING DIODE AND ORGANIC LIGHT-EMITTING DEVICE HAVING THE COMPOUND

(71) Applicant: LG Display Co., Ltd., Seoul (KR)

(72) Inventors: Jeong-Eun Baek, Paju-si (KR); Mi-Sang Yoo, Paju-si (KR); Kyung-Jin Yoon, Paju-si (KR); Joong-Hwan Yang, Paju-si (KR)

(73) Assignee: LG Display Co., Ltd., Seoul (KR)

( * ) Notice: Subject to any disclaimer, the term of this patent is extended or adjusted under 35 U.S.C. 154(b) by 513 days.

(21) Appl. No.: 16/529,107

(22) Filed: Aug. 1, 2019

(65) Prior Publication Data

US 2020/0048199 A1  Feb. 13, 2020

(30) Foreign Application Priority Data

Aug. 7, 2018 (KR) .................. 10-2018-0091756

(51) Int. Cl.
*C07D 209/82* (2006.01)
*C07D 213/06* (2006.01)
(Continued)

(52) U.S. Cl.
CPC ......... *C07D 209/82* (2013.01); *C07D 213/06* (2013.01); *C07D 219/02* (2013.01);
(Continued)

(58) Field of Classification Search
CPC .. C07D 209/82; C07D 213/06; C07D 219/02; C07D 239/26; C07D 251/16;
(Continued)

(56) References Cited

U.S. PATENT DOCUMENTS

2004/0076853 A1* 4/2004 Jarikov ............... H01L 51/5012
428/917
2004/0124766 A1* 7/2004 Nakagawa .......... H01L 51/0064
313/506
(Continued)

FOREIGN PATENT DOCUMENTS

| EP | 2243761 A1 | 10/2010 |
| JP | H10-294177 A | 11/1998 |
| WO | 2014024687 A1 | 2/2014 |

OTHER PUBLICATIONS

Extended European Search Report issued in corresponding European Patent Application No. 19190298 dated Dec. 23, 2019.
(Continued)

*Primary Examiner* — Dawn L Garrett
(74) *Attorney, Agent, or Firm* — Morgan, Lewis & Bockius LLP

(57) ABSTRACT

An organic compound having a naphtho fluoranthene core and a hetero aromatic group bonded to a specific position of the naphtho fluoranthene core, an organic light-emitting diode and an organic light-emitting device including the compound are disclosed. Since the organic compound has a narrow Stokes Shift between an absorption wavelength and an emission wavelength, the organic compound has a broad overlapped area between its absorption peak and an emission peak of a delayed fluorescent material, and therefore it can emit blue light with high color purity. It is possible to manufacture an organic light-emitting diode (OLED) and an organic light-emitting device that enhance luminous efficiency and color purity using the organic compound.

29 Claims, 11 Drawing Sheets

(51) Int. Cl.

| | |
|---|---|
| *C07D 219/02* | (2006.01) |
| *C07D 239/26* | (2006.01) |
| *C07D 307/91* | (2006.01) |
| *C07D 491/107* | (2006.01) |
| *H01L 51/00* | (2006.01) |
| *H01L 51/50* | (2006.01) |
| *C09K 11/06* | (2006.01) |
| *C07D 251/16* | (2006.01) |

(52) U.S. Cl.
CPC ......... *C07D 239/26* (2013.01); *C07D 307/91* (2013.01); *C07D 491/107* (2013.01); *C09K 11/06* (2013.01); *H01L 51/0056* (2013.01); *H01L 51/0067* (2013.01); *H01L 51/0072* (2013.01); *H01L 51/0073* (2013.01); *H01L 51/0074* (2013.01); *H01L 51/504* (2013.01); *H01L 51/5012* (2013.01); *C07D 251/16* (2013.01); *H01L 51/5056* (2013.01); *H01L 51/5096* (2013.01); *H01L 2251/5384* (2013.01)

(58) Field of Classification Search
CPC .. C07D 307/91; C07D 491/107; C09K 11/06; H01L 2251/5384; H01L 27/3244; H01L 51/0056; H01L 51/0058; H01L 51/0067; H01L 51/0072; H01L 51/0073; H01L 51/0074; H01L 51/5012; H01L 51/504; H01L 51/5056; H01L 51/5096
See application file for complete search history.

(56) References Cited

U.S. PATENT DOCUMENTS

| | | | |
|---|---|---|---|
| 2007/0292714 A1 | 12/2007 | Funahashi | |
| 2010/0187517 A1* | 7/2010 | Nishimura | ............ C09B 57/008 257/E51.026 |
| 2015/0280158 A1* | 10/2015 | Ogiwara | ............. H01L 51/5016 257/40 |
| 2016/0163997 A1* | 6/2016 | Noh | ....................... C09K 11/02 257/40 |

OTHER PUBLICATIONS

Mohammad-Pour et al., Modular Design of Fluorescent Dibenzo- and Naphtho-Fluoranthenes: Structural Rearrangements and Electronic Properties, J. Org. Chem. 83: 8036-8053 (2018).

* cited by examiner

ORGANIC COMPOUND, AND ORGANIC LIGHT-EMITTING DIODE AND ORGANIC LIGHT-EMITTING DEVICE HAVING THE COMPOUND

CROSS-REFERENCE TO RELATED APPLICATIONS

This application claims the benefit under 35 U.S.C. § 119(a) of Korean Patent Application No. 10-2018-0091756, filed in the Republic of Korea on Aug. 7, 2018, which is incorporated herein by reference in its entirety.

BACKGROUND

Technical Field

The present disclosure relates to an organic compound, and more specifically, to an organic compound enhancing luminous efficiency and color purity, an organic light-emitting diode and an organic light-emitting device including the compound.

Description of the Related Art

As a display device has become larger, there exists a need for a flat display device with lower spacing occupation. Among the flat display devices, a display device using an organic light-emitting diode (OLED) has come into the spotlight.

In the OLED, when electrical charges are injected into an emission layer between an electron injection electrode (i.e., cathode) and a hole injection electrode (i.e., anode), electrical charges are combined to be paired, and then emit light as the combined electrical charges are disappeared.

The OLED can be formed even on a flexible transparent substrate such as a plastic substrate. In addition, the OLED can be driven at a lower voltage of 10 V or less. Besides, the OLED has relatively low power consumption for driving compared to plasma display panel and inorganic electroluminescent devices, and color purity thereof is very high. Further, since the OLED can display various colors such as green, blue, red and the likes, the OLED display device has attracted a lot of attention as a next-generation display device that can replace a liquid crystal display device (LCD).

The OLED may have a mono-layered emitting material layer between the anode and the cathode. Alternatively, the OLED may have a multiple-layered emission layer that includes a hole injection layer (HIL), a hole transport layer (HTL), an emitting material layer (EML), an electron transport layer (ETL) and an electron injection layer (EIL) between the anode and the cathode so that the OLED can enhance luminous efficiency. The multiple-layered emission layer may further include an exciton blocking layer such as an electron blocking layer EBL between the HTL and the EML and/or a hole blocking layer HBL between the EML and the ETL so as to prevent the excitons from disappearing.

The EML comprises a host and a dopant, and the actual emission is carried out at the dopant. Since material used as blue dopant must have wider band energy gap compared to a green and/or red dopant, there have been difficulties in developing a blue dopant. US Patent Publication No. 2007/0292714 discloses blue luminous materials with a pyrene core and diphenyl amino substituent. However, the prior art luminous material had low luminous efficiency and short life span, showed low color purity and caused limitation in implementing full-color display.

SUMMARY

Accordingly, embodiments of the present disclosure are directed to an organic compound, an organic light-emitting diode and an organic light-emitting device including the organic compounds that substantially obviate one or more of the problems due to the limitations and disadvantages of the related art.

An aspect of the present disclosure is to provide an organic compound, an organic light-emitting diode and an organic light-emitting device that can enhance luminous efficiency and color purity.

Another aspect of the present disclosure is to provide an organic light-emitting diode and an organic light-emitting device that can lower driving voltage and power consumption, and can improve life span.

Additional features and aspects will be set forth in the description that follows, and in part will be apparent from the description, or may be learned by practice of the inventive concepts provided herein. Other features and aspects of the inventive concepts may be realized and attained by the structure particularly pointed out in the written description, or derivable therefrom, and the claims hereof as well as the appended drawings.

The abovementioned aspects are solved by the features of the independent claims. Preferred embodiments are covered by the dependent claims. To achieve these and other aspects of the inventive concepts, as embodied and broadly described, the present disclosure provides an organic compound represented by the following Chemical Formula 1:

Chemical Formula 1

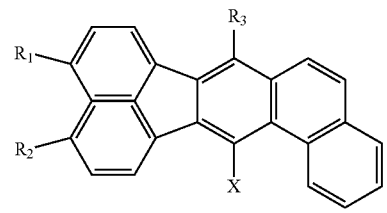

wherein each of $R_1$ to $R_3$ is independently selected from the group consisting of hydrogen, unsubstituted or substituted $C_1$~$C_{10}$ alkyl group, unsubstituted or substituted $C_5$~$C_{30}$ aromatic group; and X is an unsubstituted or a substituted $C_4$~$C_{30}$ hetero aromatic group.

Preferably, X is a $C_4$~$C_{30}$ hetero aromatic group unsubstituted or substituted with at least one of a $C_1$~$C_{10}$ alkyl group and a $C_4$~$C_{30}$ aromatic or a hetero aromatic group.

The $C_4$~$C_{30}$ hetero aromatic group is preferably selected from the group consisting of $C_4$~$C_{30}$ hetero aryl group, $C_4$~$C_{30}$ hetero aralkyl group, $C_4$~$C_{30}$ hetero aryloxyl group and $C_4$~$C_{30}$ hetero aryl amino group, and each of the hetero aryl group, the hetero aralkyl group, the hetero aryloxyl group and the hetero aryl amino group is independently unsubstituted or substituted with at least one of a $C_1$~$C_{10}$ alkyl group and a $C_4$~$C_{30}$ aromatic or a hetero aromatic group.

Preferably, each of $R_1$ to $R_3$ is independently selected from the group consisting of hydrogen, methyl group, tert-butyl group, phenyl group and naphthyl group.

It is further preferred, if X has any of the following structures:
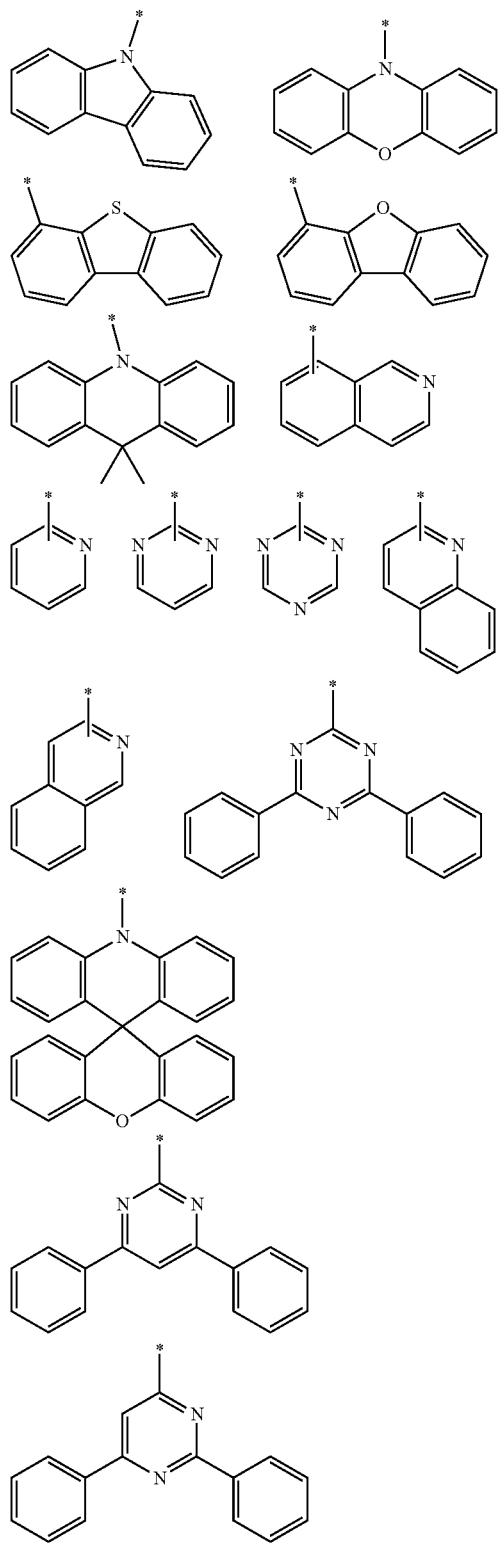
wherein the asterisk indicates a bonded portion.
In another preferred embodiment, the organic compound has one of the following structures of Chemical Formula 2:
Chemical Formula 2
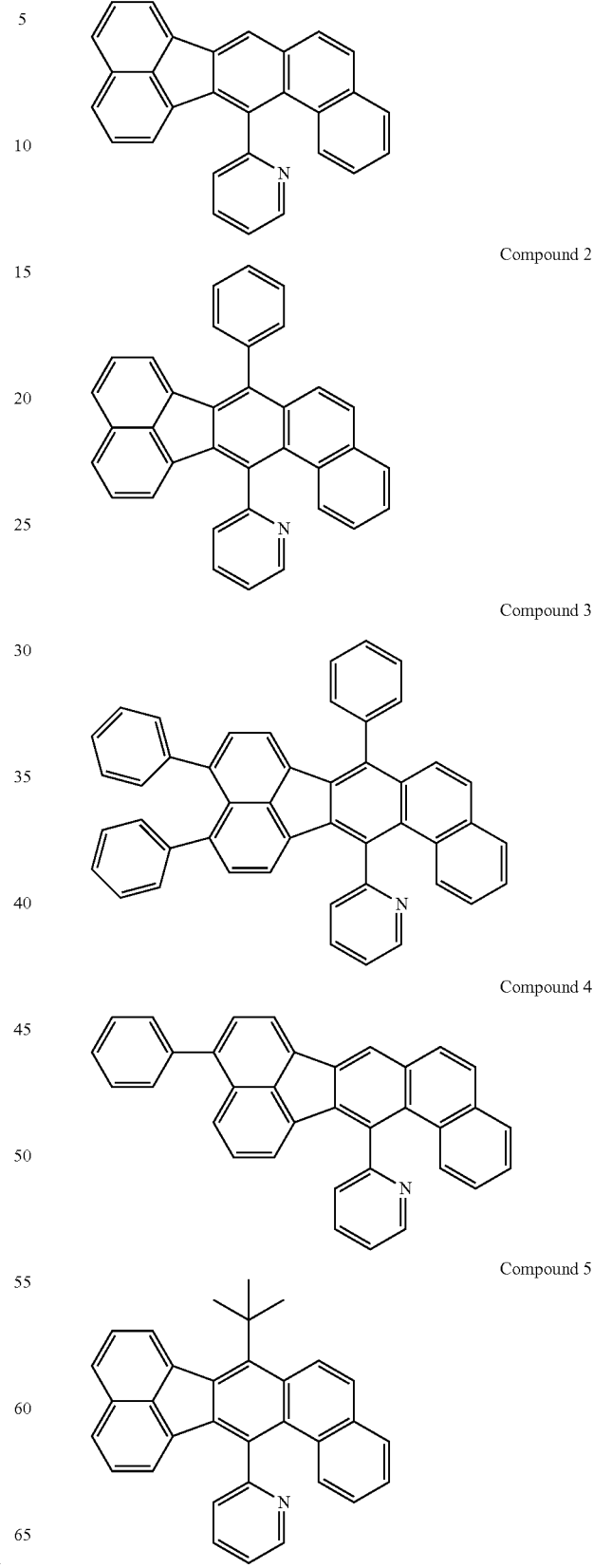
Compound 1
Compound 2
Compound 3
Compound 4
Compound 5

Compound 6
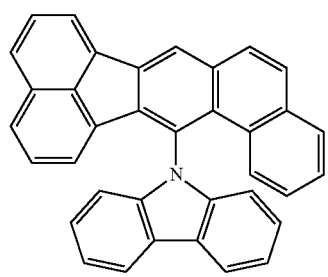
Compound 7
Compound 8
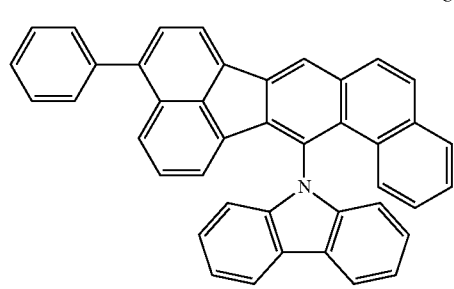
Compound 9
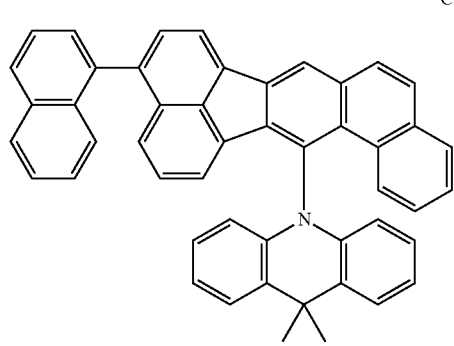
Compound 10
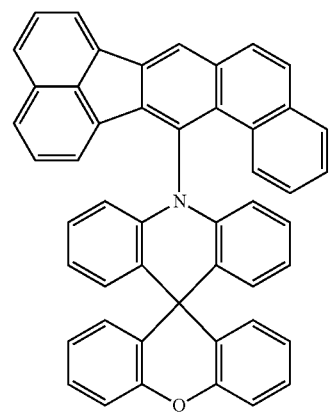
Compound 11
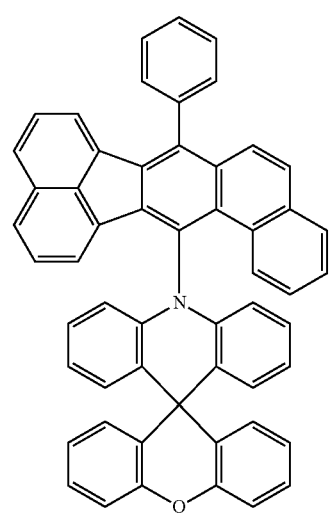
Compound 12
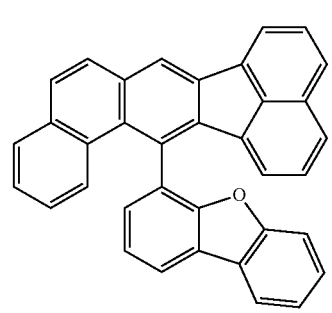
Compound 13

-continued
Compound 14
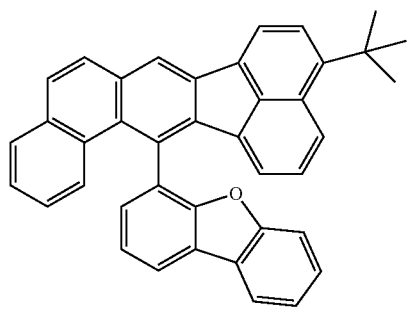
Compound 15
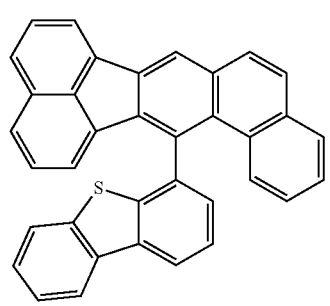
Compound 16
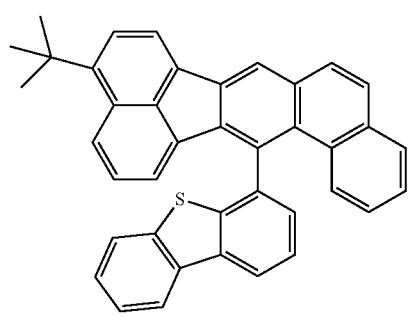
Compound 17
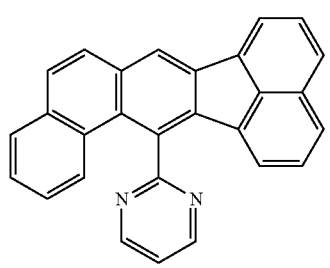
Compound 18
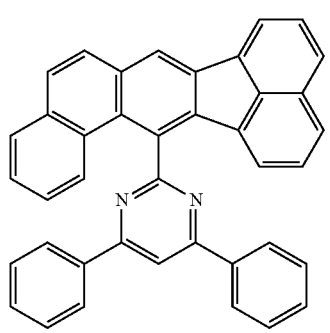
-continued
Compound 19
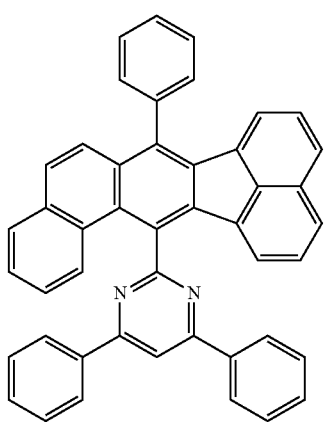
Compound 20
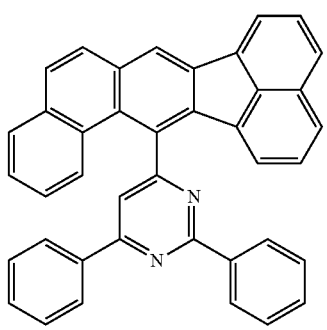
Compound 21
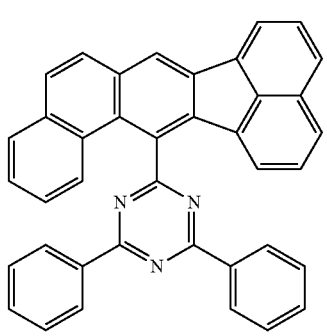
Compound 22
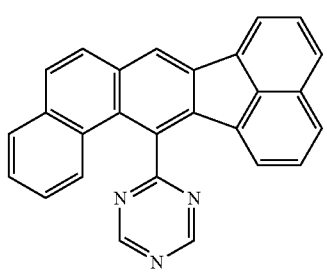

Compound 23

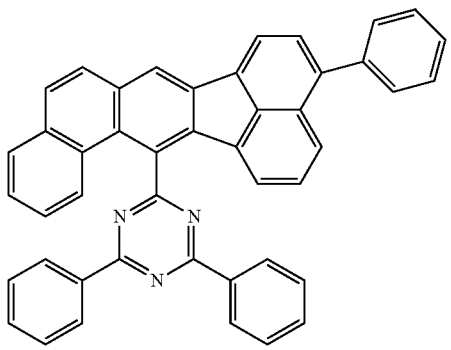

In another aspect, the present disclosure provides an organic light-emitting diode (OLED) that comprises a first electrode; a second electrode facing the first electrode; and a first emitting material layer between the first and second electrode, wherein the first emitting material layer comprises the above organic compound.

The first emitting material layer preferably further includes a first host and a first dopant, wherein the organic compound is used as a second dopant.

An excited state singlet energy level of the first dopant is preferably higher than an excited state singlet energy level of the second dopant.

An excited state triplet energy level of the first dopant is preferably lower than an excited state triplet energy level of the first host and higher than an excited state triplet energy level of the second dopant.

Preferably, an energy bandgap between an excited state single energy level of the first dopant and an excited state triplet energy level of the first dopant is equal to or less than about 0.3 eV.

It is further preferred, if an energy bandgap between a Highest Occupied Molecular Orbital energy level of the first host and a Highest Occupied Molecular Orbital energy level of the first dopant or an energy bandgap between a Lowest Unoccupied Molecular Orbital energy level of the first host and a Lowest Unoccupied Molecular Orbital energy level of the first dopant is equal to or less than about 0.5 eV.

In another embodiment, the first emitting material layer further includes a first host, wherein the organic compound is used as a first fluorescent dopant.

In this case, it is preferred that the diode further comprising a second emitting material layer between the first electrode and the first emitting material layer or between the first emitting material layer and the second electrode, wherein the second emitting material layer includes a second host and a delayed fluorescent dopant.

The second emitting material layer is preferably disposed between the first emitting material layer and the second electrode. In this case, the diode preferably further comprises an electron blocking layer between the first electrode and the first emitting material layer. The first host is, in particular, formed of the same material as the electron blocking layer.

In another embodiment, the second emitting material layer is disposed between the first electrode and the first emitting material layer. In this case the diode preferably further comprises a hole blocking layer between the first emitting material layer and the second electrode. The first host is, in particular, formed of the same material as the hole blocking layer.

Preferably, an excited state singlet energy level of the delayed fluorescent dopant is higher than an excited state singlet energy level of the first fluorescent dopant.

Further, an excited state singlet energy level of the first host may be higher than an excited state singlet energy level of the first fluorescent dopant, and each of an excited state singlet energy level and an excited state triplet energy level of the second host may be respectively higher than an excited state singlet energy level and an excited state triplet energy level of the delayed fluorescent dopant.

The diode may further comprise a third emitting material layer disposed oppositely to the first emitting material layer with respect to the second emitting material layer, wherein the third emitting material layer preferably includes a third host and a second fluorescent dopant.

Preferably, the second emitting material layer is disposed between the first emitting material layer and the second electrode, and the third emitting material layer is disposed between the second emitting material layer and the second electrode.

The diode preferably further comprises an electron blocking layer between the first electrode and the first emitting material layer. In this case, the first host is, in particular, formed of the same material as the electron blocking layer.

Alternatively, the diode further comprises a hole blocking layer between the third emitting material layer and the second electrode. In this case, the third host is, in particular, formed of the same material as the hole blocking layer.

An excited state singlet energy level of the delayed fluorescent dopant may be higher than an excited state singlet energy level of the first fluorescent dopant and an excited state singlet energy level of the second fluorescent dopant.

Preferably, an excited state singlet energy level of the first host is higher than an excited state singlet energy level of the first fluorescent dopant, each of an excited state singlet energy level and an excited state singlet energy level and an excited state triplet energy level of the second host is respectively higher than an excited state singlet energy level and an excited state triplet energy level of the delayed fluorescent dopant, and an excited state singlet energy level of the third host is higher than an excited state singlet energy level of the second fluorescent dopant.

In still another aspect, the present disclosure provides an organic light-emitting device that comprises a substrate and the OLED disposed over the substrate, as described above.

Preferably, the organic light-emitting device comprises an organic light-emitting display device and an organic light-emitting illumination device.

It is to be understood that both the foregoing general description and the following detailed description are examples and are explanatory and are intended to provide further explanation of the disclosure as claimed.

BRIEF DESCRIPTION OF THE DRAWINGS

The accompanying drawings, which are included to provide a further understanding of the disclosure and are incorporated in and constitute a part of this application, illustrate embodiments of the disclosure and together with the description serve to explain various principles. In the drawings.

DETAILED DESCRIPTION

Figure 1:
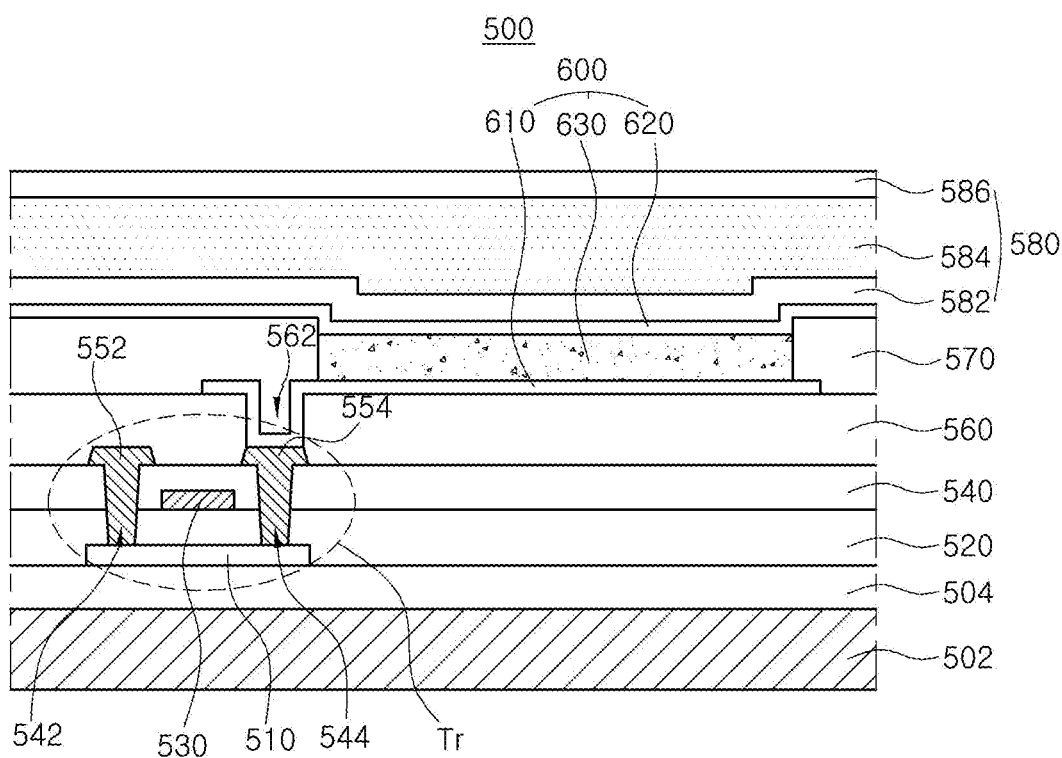
FIG. 1 is a schematic cross-sectional view illustrating an organic light-emitting display device of the present disclosure.

Reference will now be made in detail to aspects of the disclosure, examples of which are illustrated in the accompanying drawings.

Organic Compound

An organic compound of the present disclosure has a rigid naphtho fluoranthene core and a hetero aromatic group bonded at a specific position of the naphtho fluoranthene core. The organic compound of the present disclosure may be represented by the following Chemical Formula 1:

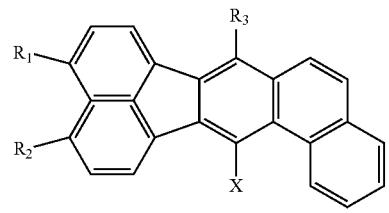

In Chemical Formula 1, each of $R_1$ to $R_3$ is independently selected from the group consisting of hydrogen, unsubstituted or substituted $C_1$~$C_{10}$ alkyl group, unsubstituted or substituted $C_5$~$C_{30}$ aromatic group.

X is an unsubstituted or a substituted $C_4$~$C_{30}$ hetero aromatic group.

As used herein, the term "unsubstituted" means that a hydrogen atom is bonded, and in this case the hydrogen atom comprises a protium, deuterium and tritium.

As used herein, the term "hetero" described in "hetero aromatic ring", "hetero aromatic group", "hetero alicyclic ring", "hetero cyclic alkyl group", "hetero aryl group", "hetero aralkyl group", "hetero aryloxyl group", "hetero aryl amino group", "hetero arylene group", "hetero aralkylene group", "hetero aryloxylene group", and the likes means that at least one carbon atom, for example 1 to 5 carbon atoms, forming such aromatic or alicyclic rings are substituted with at least one hetero atom selected from the group consisting of N, O, S and combinations thereof.

In one embodiment, the $C_5$~$C_{30}$ aromatic group of $R_1$ to $R_3$ may comprise, but is not limited to, unsubstituted or substituted $C_5$~$C_{30}$ aryl group, unsubstituted or substituted $C_5$~$C_{30}$ aralkyl group, unsubstituted or substituted $C_5$~$C_{30}$ aryloxyl group and/or unsubstituted or substituted $C_5$~$C_{30}$ aryl amino group. For example, the $C_5$~$C_{30}$ aryl group of $R_1$ to $R_3$ may comprise, but is not limited to, a non-fused or fused aromatic group such as phenyl, biphenyl, terphenyl, tetraphenyl, naphthyl, anthracenyl, indenyl, phenalenyl, phenanthrenyl, azulenyl, pyreneyl, fluorenyl, tetracenyl, indacenyl or spiro fluorenyl, each of which may be unsubstituted or substituted.

In another embodiment, the $C_4$~$C_{30}$ hetero aromatic group of X may comprise, but is not limited to, a $C_4$~$C_{30}$ hetero aromatic group unsubstituted or substituted with at least one of a $C_1$~$C_{10}$ alkyl group and a $C_4$~$C_{30}$ aromatic or hetero aromatic group. For example, the $C_4$~$C_{30}$ hetero aromatic group of X may be selected from, but is not limited to, the group consisting of a $C_4$~$C_{30}$ hetero aryl group, a $C_4$~$C_{30}$ hetero aralkyl group, a $C_4$~$C_{30}$ hetero aryloxyl group and a $C_4$~$C_{30}$ hetero aryl amino group. In this case, each of the hetero aryl group, the hetero aralkyl group, the hetero aryloxyl group and the hetero aryl amino group may be independently unsubstituted or substituted with at least one of a $C_1$~$C_{10}$ alkyl group and a $C_4$~$C_{30}$ aromatic or hetero aromatic group.

For example, the $C_4$~$C_{30}$ hetero aromatic group of X may comprise, but is not limited to, unfused or fused hetero aromatic group such as furanyl, thiophenyl, pyrrolyl, pyridyl, pyridinyl, pyrimidyl, pyrimidinyl, pyrazinyl, pyridazinyl, triazinyl, tetrazinyl, imidazolyl, pyrazolyl, indolyl, carbazolyl, benzocarbazolyl, dibenzocarbazolyl, indolocarbazolyl, indenocarbazolyl, benzofurannocarbazolyl, benzothienocarbazolyl, quinolinyl, iso-quinolinyl, phthalazinly, quinoxalinyl, cinnolinyl, quinazolinyl, benzoquinolinyl, beznoiso-quinolinyl, benzoquinoxalinyl, benzoquinazolinyl, acridinyl, phenanthrolyl, pyranyl, oxazinyl, oxazolyl, iso-oxazolyl, oxadiazolyl, triazolyl, dioxinyl, benzofuranyl, dibenzofuranyl, thiopyranyl, thiazinyl, benzothiophenyl, dibenzothiophenyl, thiazolyl, iso-thiazolyl, xanthenyl, spiro-xanthenyl, acridinyl, dihydro-acridinyl substituted with at least one $C_1$~$C_{10}$ alkyl group, spiro-acridinyl, phenazinyl, spiro-phenazinyl, thiophenzinyl, spiro-thiophenazinyl, phenoxazinyl, thisphenzinyl, and the likes.

In one embodiment, the $C_4$~$C_{30}$ aromatic or hetero aromatic group, which may be substituted with X, may comprise, but is not limited to, a $C_5$~$C_{30}$ aryl group, a $C_4$~$C_{30}$ hetero aryl group, a $C_5$~$C_{30}$ aralkyl group, a $C_4$~$C_{30}$ hetero aralkyl group, a $C_5$~$C_{30}$ aryloxyl group, a $C_4$~$C_{30}$ hetero aryloxyl group, a $C_5$~$C_{30}$ aryl amino group and/or a $C_4$~$C_{30}$ hetero aryl amino group. For example, the $C_4$~$C_{30}$ aromatic or hetero aromatic group, which may be substituted with X, may comprise, but is not limited to, the aryl group such as phenyl and the likes of $R_1$ to $R_3$, or the hetero aryl group such as furanyl, and the likes of X. In one embodiment, X may be a radical for adjusting color sensitivity of the organic compound represented by Chemical Formula 1.

In this case, when the number of the aromatic or hetero aromatic rings forming respectively $R_1$ to $R_3$ and/or X in Chemical Formula 1 becomes larger, the whole organic compound may have extremely long conjugated structures, and therefore, its energy band gap may be extremely lowered. For example, each of $R_1$ to $R_3$ and/or X may include 1-3 rings, preferably 1-2 rings, and more preferably a single ring. Besides, each of $R_1$ to $R_3$ and/or X may be respectively a 5-membered ring, a 6-membered ring or a 7-membered ring, preferably a 6-membered ring, so that the organic compound may enhance charge transfer property.

The organic compound represented by Chemical Formula 1 has a rigid structure of naphtho fluoranthene core and a hetero aromatic group X bonded to a specific position sterically adjacent to a conformationally bent naphtho moiety in the naphtho fluoranthene core, and therefore, it has maximal steric hindrance.

Accordingly, as the organic compound can exhibit small Stokes Shift, which is a difference between UV wavelength of maximum absorption (UV $\lambda_{max}$) and wavelength of maximum photoluminescence (PL $\lambda_{max}$), it can emit blue color with high color purity. Particularly, it is possible to implement hyper fluorescence with enhanced luminous efficiency and improved color purity by using the organic compound in an emission layer of an organic light-emitting diode, as described below. Since the organic compound represented by Chemical Formula 1 has a conformationally rigid spiro anthracene core bonded by an aromatic amino group and/or an aromatic or hetero aromatic group at specific positions, it can enhance its color purity. Particularly, it is possible to implement a light-emitting diode or device that has a low driving voltage and an enhanced luminous efficiency using the organic compound according to the present disclosure. For example, the organic compound according to the present disclosure may be used as a dopant in an emitting material layer of an organic light-emitting diode.

In an exemplary embodiment, each of $R_1$ to $R_3$ in Chemical Formula 1 may be independently selected from, but is not limited to, the group consisting of hydrogen, methyl group, tert-butyl group, phenyl group and naphthyl group. In an alternatively exemplary embodiment, X in Chemical Formula 1 may have any one of the following structures:

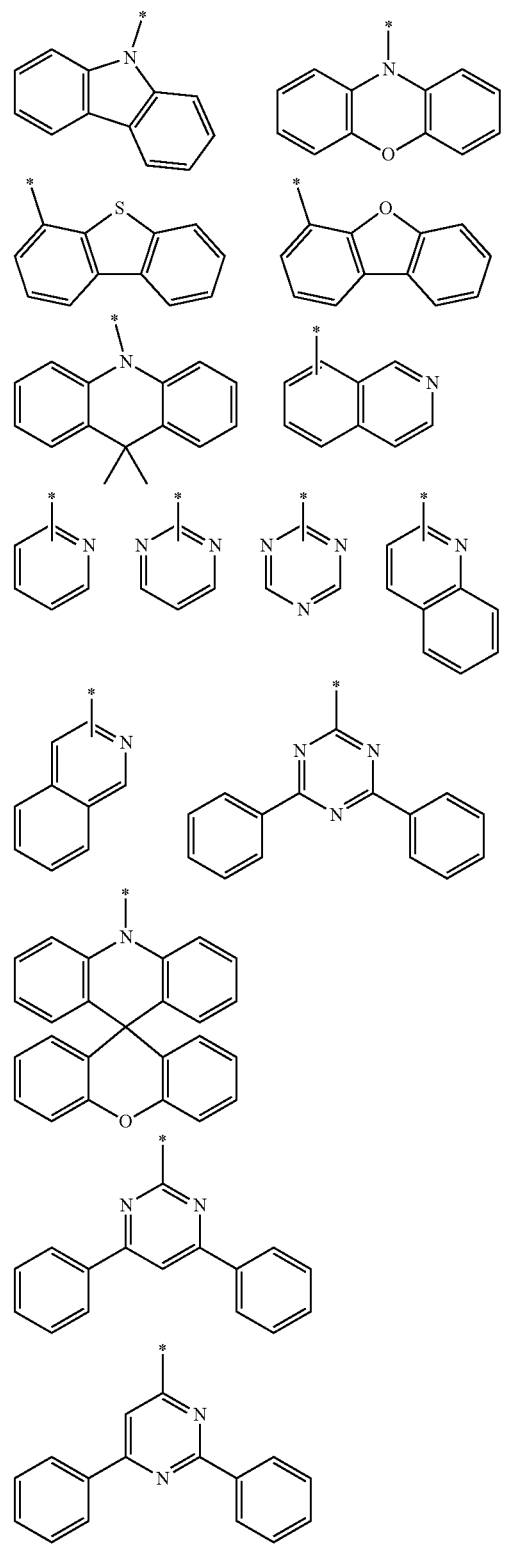

wherein the asterisk indicates a bonded portion.

As an example, each of $R_1$ and $R_2$ in Chemical Formula 1 may comprise independently, but is not limited to, hydrogen, $C_1$-$C_5$ alkyl (e.g. methyl, ethyl, propyl, iso-propyl, butyl, iso-butyl, tert-butyl, pentyl, iso-pentyl or tert-pentyl), phenyl and naphthyl. $R_3$ in Chemical Formula 1 may comprise, but is not limited to, hydrogen, $C_1$~$C_5$ alkyl (e.g. methyl, ethyl, propyl, iso-propyl, butyl, iso-butyl, tert-butyl, pentyl, iso-pentyl or tert-pentyl) and phenyl. X in Chemical Formula 1 may comprise, but is not limited to, pyridyl, carbazolyl, acridinyl, dihydro acridinyl unsubstituted or substituted with at least one alkyl (e.g. dimethyl), spiro [acridine-9,9'-xanthenyl, dibenzofuranyl, dibenzothienyl, pyrimidinyl unsubstituted or substituted with at least one phenyl, triazinyl unsubstituted or substituted with at least one phenyl. Particularly, the organic compound represented by Chemical Formula 1 may have any one of the following structures of Chemical Formula 2:

Chemical Formula 2

Compound 1

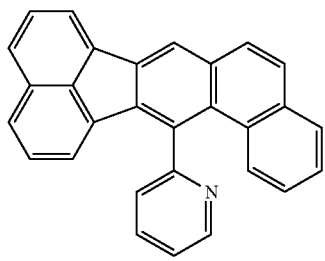

Compound 2

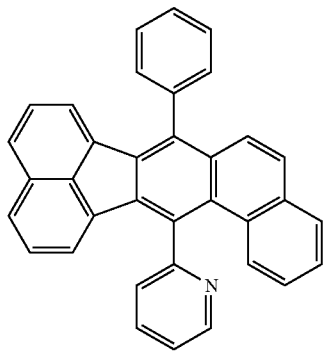

Compound 3

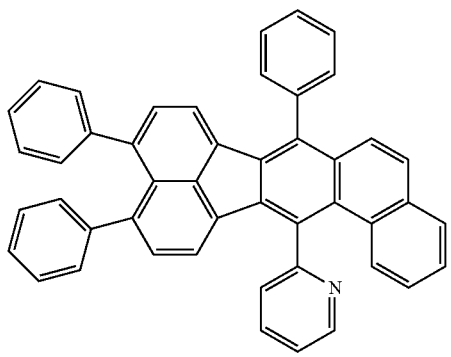

Compound 4

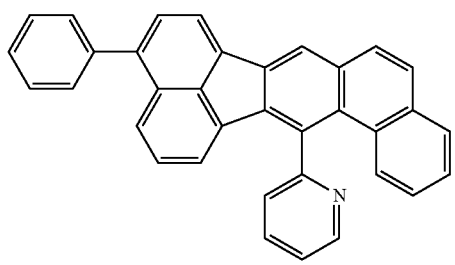

Compound 5

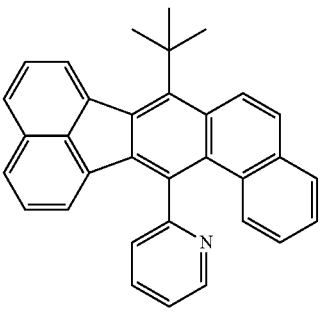

Compound 6

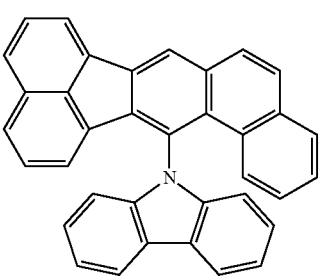

Compound 7

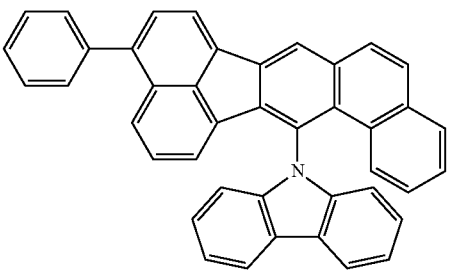

Compound 8

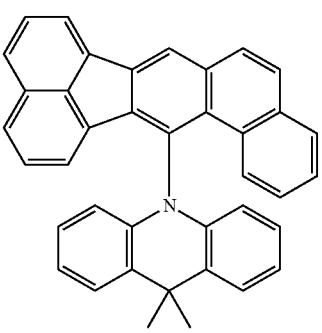

Compound 9

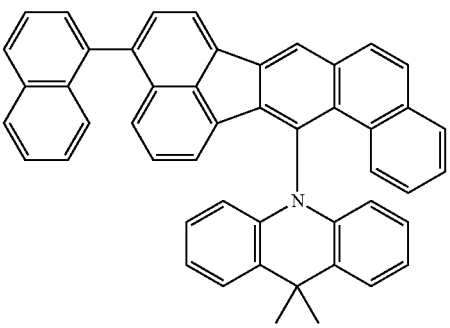

Compound 10
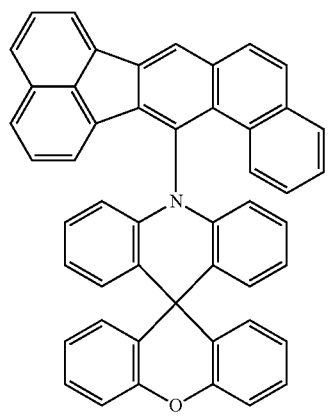
Compound 11
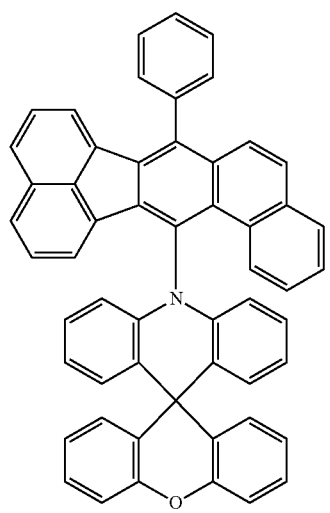
Compound 12
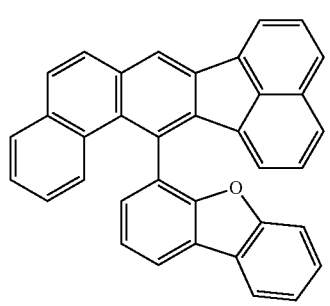
Compound 13
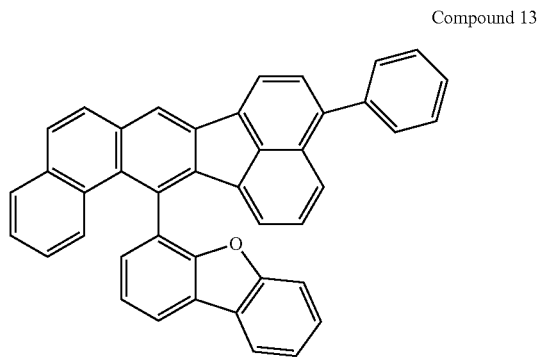
Compound 14
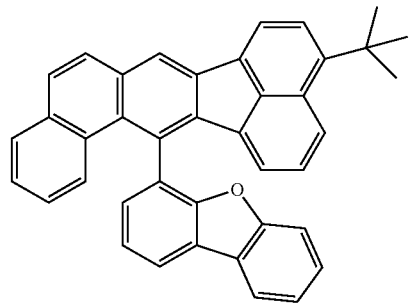
Compound 15
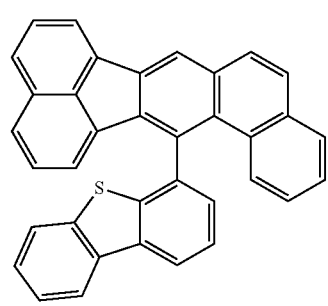
Compound 16
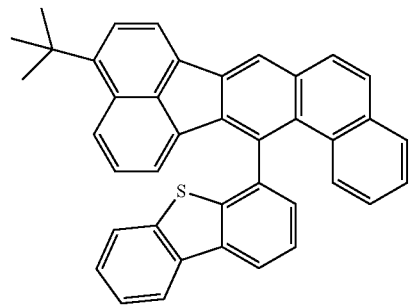
Compound 17
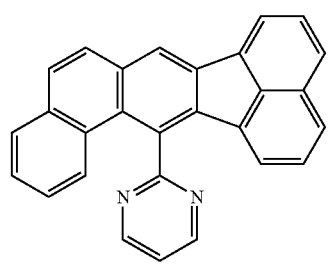
Compound 18
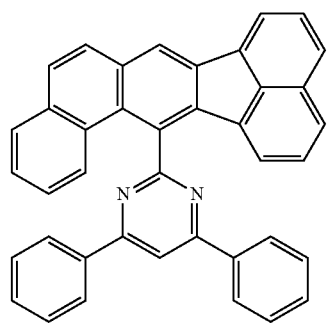

-continued

Compound 19

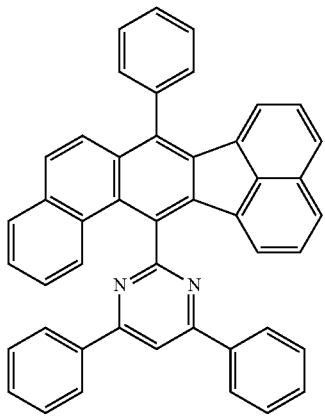

Compound 20

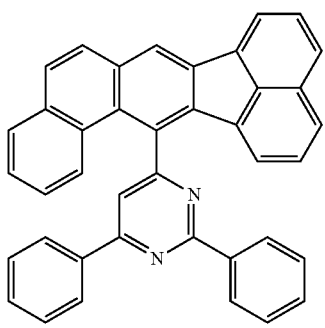

Compound 21

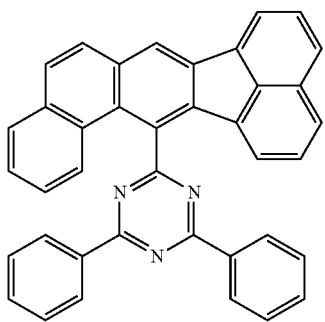

Compound 22

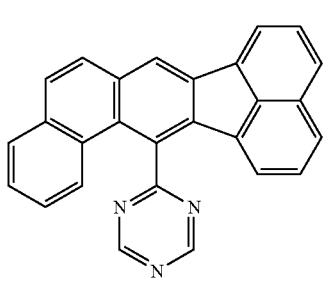

-continued

Compound 23

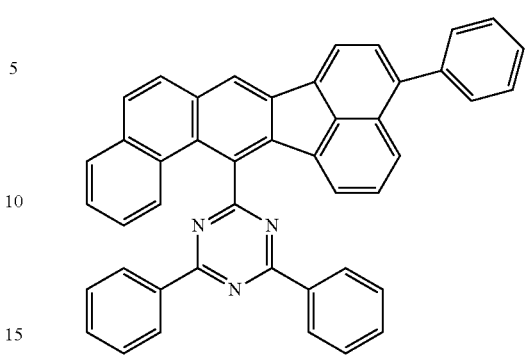

Each of the organic compounds represented by the above Chemical Formula 2 has a naphtho fluoranthene core and a hetero aromatic group, for adjusting color sensitivity, bonded to a specific position sterically adjacent to a conformationally bent naphtho moiety in the naphtho fluoranthene core. Since each of the organic compounds represented by Chemical Formula 2 has a narrow Stokes Shift, its wavelength of maximum photoluminescence moves toward much longer wavelengths. The organic compound has a broader absorption wavelength range which overlaps with an emission wavelength range of the delayed fluorescent material than an absorption wavelength range of the prior art fluorescent materials, and energy is transferred efficiently from the delayed fluorescent material to the organic compound. Therefore, it is possible to enhance luminous efficiency of an organic light-emitting diode by using the organic compound represented by Chemical Formula 2 as the fluorescent dopant and implement blue emission with high color purity.

[Organic Light-Emitting Diode and Device]

As explained above, the organic compound represented by the Chemical Formulae 1 to 2 may be applied to an emitting material layer of an organic light-emitting diode which has high color purity and high luminous efficiency. The organic light-emitting diode of the present disclosure may be applied to an organic light-emitting device such as an organic light-emitting display device and an organic light-emitting illumination device. A display device having the organic light-emitting diode of the present disclosure will be explained. FIG. 1 is a schematic cross-sectional view illustrating an organic light-emitting display device of the present disclosure.

As illustrated in FIG. 1, the organic light-emitting display device 500 comprises a substrate 502, a thin-film transistor Tr on the substrate 502, and an organic light-emitting diode 600 connected to the thin film transistor Tr.

The substrate 502 may include, but is not limited to, glass, thin flexible material and/or polymer plastics. For example, the flexible material may be selected from the group, but is not limited to, polyimide (PI), polyethersulfone (PES), polyethylenenaphthalate (PEN), polyethylene terephthalate (PET), polycarbonate (PC) and combination thereof. The thin film transistor Tr, and the substrate 502, over which the organic light-emitting diode 600 is arranged, form an array substrate.

A buffer layer 504 may be disposed over the substrate 502, and the thin film transistor Tr is disposed over the buffer layer 504. The buffer layer 504 may be omitted.

A semiconductor layer 510 is disposed over the buffer layer 504. In one exemplary embodiment, the semiconductor layer 510 may comprise oxide semiconductor materials. In this case, a light-shield pattern (not shown) may be disposed under the semiconductor layer 510, and the light-shield pattern (not shown) can prevent light from being incident toward the semiconductor layer 510, and thereby, preventing the semiconductor layer 510 from being deteriorated by the light. Alternatively, the semiconductor layer 510 may comprise polycrystalline silicon. In this case, opposite edges of the semiconductor layer 510 may be doped with impurities.

A gate insulating layer 520 formed of an insulating material is disposed on the semiconductor layer 510. The gate insulating layer 520 may comprise an inorganic insulating material such as silicon oxide ($SiO_x$) or silicon nitride ($SiN_x$).

A gate electrode 530 made of a conductive material such as a metal is disposed over the gate insulating layer 520 so as to correspond to a center of the semiconductor layer 510. While the gate insulating layer 520 is disposed over a whole area of the substrate 502 in FIG. 1, the gate insulating layer 520 may be patterned identically as the gate electrode 530.

An interlayer insulating layer 540 formed of an insulating material is disposed on the gate electrode 530 with covering over an entire surface of the substrate 502. The interlayer insulating layer 540 may comprise, but is not limited to, an inorganic insulating material such as silicon oxide ($SiO_x$) or silicon nitride ($SiN_x$), or an organic insulating material such as benzocyclobutene or photo-acryl.

The interlayer insulating layer 540 has first and second semiconductor layer contact holes 542 and 544 that expose both top sides of the semiconductor layer 510. The first and second semiconductor layer contact holes 542 and 544 are disposed over opposite sides of the gate electrode 530 with spacing apart from the gate electrode 530. The first and second semiconductor layer contact holes 542 and 544 are formed within the gate insulating layer 520 in FIG. 1. Alternatively, the first and second semiconductor layer contact holes 542 and 544 are formed only within the interlayer insulating layer 540 when the gate insulating layer 520 is patterned identically as the gate electrode 530.

A source electrode 552 and a drain electrode 554, which are formed of a conductive material such as a metal, are disposed on the interlayer insulating layer 540. The source electrode 552 and the drain electrode 554 are spaced apart from each other with respect to the gate electrode 530, and contact both sides of the semiconductor layer 510 through the first and second semiconductor layer contact holes 542 and 544, respectively.

The semiconductor layer 510, the gate electrode 530, the source electrode 552 and the drain electrode 554 constitute the thin film transistor Tr, which acts as a driving element. The thin film transistor Tr in FIG. 1 has a coplanar structure in which the gate electrode 530, the source electrode 552 and the drain electrode 554 are disposed over the semiconductor layer 510. Alternatively, the thin film transistor Tr may have an inverted staggered structure in which a gate electrode is disposed under a semiconductor layer and a source and drain electrodes are disposed over the semiconductor layer. In this case, the semiconductor layer may comprise amorphous silicon.

Although not shown in FIG. 1, a gate line and a data line, which cross each other to define a pixel region, and a switching element, which is connected to the gate line and the data line is, may be further formed in the pixel region. The switching element is connected to the thin film transistor Tr, which is a driving element. Besides, a power line is spaced apart in parallel from the gate line or the data line, and the thin film transistor Tr may further include a storage capacitor configured to constantly keep a voltage of the gate electrode for one frame.

In addition, the organic light-emitting display device 500 may include a color filter (not shown) for absorbing a part of the light emitted from the organic light-emitting diode 600. For example, the color filter (not shown) may absorb a light of specific wavelength such as red (R), green (G) or blue (B). In this case, the organic light-emitting display device 500 can implement full-color through the color filter (not shown).

For example, when the organic light-emitting display device 500 is a bottom-emission type, the color filter (not shown) may be disposed on the interlayer insulating layer 540 with corresponding to the organic light-emitting diode 600. Alternatively, when the organic light-emitting display device 500 is a top-emission type, the color filter (not shown) may be disposed over the organic light-emitting diode 600, that is, a second electrode 620.

A passivation layer 560 is disposed on the source and drain electrodes 552 and 554 over the whole substrate 502. The passivation layer 560 has a flat top surface and a drain contact hole 562 that exposes the drain electrode 554 of the thin film transistor Tr. While the drain contact hole 562 is disposed on the second semiconductor layer contact hole 554, it may be spaced apart from the second semiconductor layer contact hole 554.

The organic light-emitting diode 600 includes a first electrode 610 that is disposed on the passivation layer 560 and connected to the drain electrode 554 of the thin film transistor Tr. The organic light-emitting diode 600 further includes an emission layer 630 and a second electrode 620 each of which is disposed sequentially on the first electrode 610.

The first electrode 610 is disposed in each pixel region. The first electrode 610 may be an anode and include a conductive material having a relatively high work function value. For example, the first electrode 610 may include, but is not limited to, a transparent conductive material such as indium tin oxide (ITO), indium zinc oxide (IZO), indium tin zinc oxide (ITZO), SnO, ZnO, indium cerium oxide (ICO), aluminum doped zinc oxide (AZO), and the likes.

In one exemplary embodiment, when the organic light-emitting display device 500 is a top-emission type, a reflective electrode or a reflective layer (not shown) may be disposed under the first electrode 610. For example, the reflective electrode or the reflective layer (not shown) may include, but is not limited to, an aluminum-palladium-copper (APC) alloy.

In addition, a bank layer 570 is disposed on the passivation layer 560 in order to cover edges of the first electrode 610. The bank layer 570 exposes a center of the first electrode 610.

An emission layer 630 is disposed on the first electrode 610. In one exemplary embodiment, the emission layer 630 may have a mono-layered structure of an emitting material layer. Alternatively, the emission layer 630 may have a multiple-layered structure of a hole injection layer, a hole transport layer, an electron blocking layer, an emitting material layer, a hole blocking layer, an electron transport layer and/or an electron injection layer (See, FIGS. 2, 4, 9, 10 and 12). The emission layer 630 includes the organic compound represented by any of Chemical Formulae 1 to 2. For example, the organic compound represented by any of Chemical Formulae 1 to 2 may be used as a dopant of the emission layer 630, and the emission layer 630 may include a host and other dopants.

The second electrode 620 is disposed over the substrate 502 above which the emission layer 630 is disposed. The second electrode 620 may be disposed over a whole display area and may include a conductive material with a relatively low work function value compared to the first electrode 610. The second electrode 620 may be a cathode. For example, the second electrode 620 may include, but is not limited to, aluminum (Al), magnesium (Mg), calcium (Ca), silver (Ag), alloys or combinations thereof such as an aluminum-magnesium alloy (Al—Mg).

In addition, an encapsulation film 580 may be disposed over the second electrode 620 in order to prevent outer moisture from penetrating into the organic light-emitting diode 600. The encapsulation film may have, but is not limited to, a laminated structure of a first inorganic insulating film 582, an organic insulating film 584 and a second inorganic insulating film 586.

The emission layer 630 of the organic light-emitting diode 600 may include the organic compound represented by any of Chemical Formulae 1 to 2 as a dopant, as described above. Such an organic compound has a conformationally stable naphtho fluoranthene core and a hetero aromatic group bonded at a specific position of the naphtho fluoranthene core. It is possible to manufacture the organic light emitting diode 600 and an organic light-emitting display device 500 that can enhance their color purity and luminous efficiency as well as improve their luminous life span.

Figure 2:
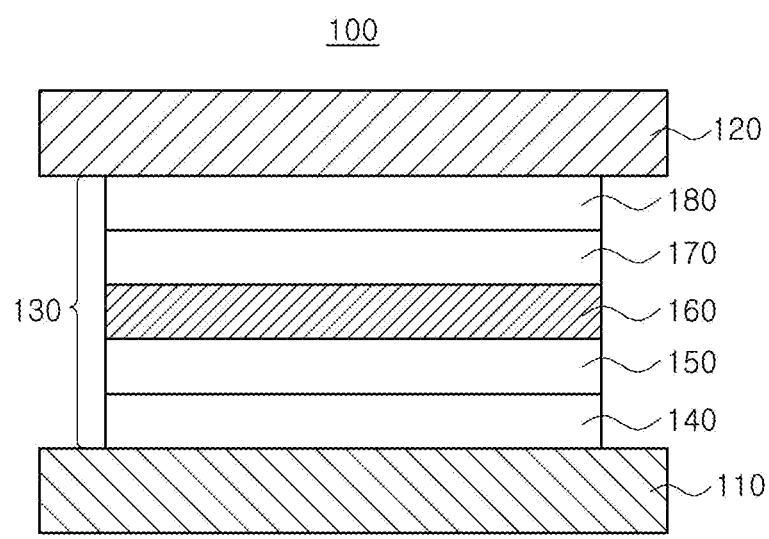
FIG. 2 is a schematic cross-sectional view illustrating an organic light-emitting diode in accordance with an exemplary embodiment of the present disclosure.

FIG. 2 is a schematic cross-sectional view illustrating an organic light-emitting diode having an organic compound as a fluorescent dopant in a single EML in accordance with an exemplary embodiment of the present disclosure.

As illustrated in FIG. 2, the organic light-emitting diode (OLED) 100 in accordance with an exemplary embodiment of the present disclosure includes first and second electrodes 110 and 120 facing each other, an emission layer 130 disposed between the first and second electrodes 110 and 120. In one exemplary embodiment, the emission layer 130 include a hole injection layer (HIL) 140, a hole transport layer (HTL) 150, an emitting material layer (EML) 160, an electron transport layer (ETL) 170 and an electron injection layer (EIL) 180 each of which is laminated sequentially from the first electrode 110.

The first electrode 110 may be an anode that provides a hole into the EML 160. As described above, the first electrode 110 may include a conductive material having a relatively high work function value, for example, a transparent conductive oxide (TCO). In an exemplary embodiment, the first electrode 110 may include, but is not limited to, ITO, IZO, ITZO, SnO, ZnO, ICO, AZO, and the likes.

The second electrode 120 may be a cathode that provides an electron into the EML 160. As described above, the second electrode 120 may include a conductive material having a relatively low work function values, i.e., a highly reflective material such as Al, Mg, Ca, Ag, alloys thereof, combinations thereof, and the likes.

The HIL 140 is disposed between the first electrode 110 and the HTL 150 and improves an interface property between the inorganic first electrode 110 and the organic HTL 150. In one exemplary embodiment, the HIL 140 may include, but is not limited to, 4,4'4"-Tris(3-methylphenylamino)triphenylamine (MTDATA), 4,4',4"-Tris(N,N-diphenyl-amino)triphenylamine (NATA), 4,4',4"-Tris(N-(naphthalene-1-yl)-N-phenyl-amino)triphenylamine (1T-NATA), 4,4',4"-Tris(N-(naphthalene-2-yl)-N-phenyl-amino) triphenylamine (2T-NATA), Copper phthalocyanine (CuPc), Tris(4-carbazoyl-9-yl-phenyl)amine (TCTA), N,N'-Diphenyl-N,N'-bis(1-naphthyl)-1,1'-biphenyl-4,4"-diamine (NPB; NPD), 1,4,5,8,9,11-Hexaazatriphenylenehexacarbonitrile (Dipyrazino[2,3-f:2'3'-h]quinoxaline-2,3,6,7,10,11-hexacarbonitrile; HAT-CN), 1,3,5-tris[4-(diphenylamino)phenyl] benzene (TDAPB), poly(3,4-ethylenedioxythiphene)polystyrene sulfonate (PEDOT/PSS) and/or N-(biphenyl-4-yl)-9,9-dimethyl-N-(4-(9-phenyl-9H-carbazol-3-yl)phenyl)-9H-fluoren-2-amine. The HIL 140 may be omitted in accordance with one embodiment of the inventive OLED 100.

The HTL 150 is disposed adjacently to the EML 160 between the first electrode 110 and the EML 160. In one exemplary embodiment, the HTL 150 may include, but is not limited to, N,N'-Diphenyl-N,N'-bis(3-methylphenyl)-1,1'-biphenyl-4,4'-diamine (TPD), NPB, 4,4'-bis(N-carbazolyl)-1,1'-biphenyl (CBP), Poly[N,N'-bis(4-butylphenyl)-N,N'-bis(phenyl)-benzidine] (Poly-TPD), Poly[(9,9-dioctylfluorenyl-2,7-diyl)-co-(4,4'-(N-(4-sec-butylphenyl) diphenylamine))] (TFB), Di-[4-(N,N-di-p-tolyl-amino)-phenyl]cyclohexane (TAPC), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The EML 160 may include a host and a dopant. In this exemplary embodiment, the EML 160 may include a host (a first host) and the organic compound represented by any of Chemical Formulae 1 to 2 as a fluorescent dopant (a first fluorescent dopant). The EML 160 may include the fluorescent dopant by about 1 to about 50% by weight and can emit blue color.

The host of the EML 160 may include, but is not limited to, 9-(3-(9H-carbazol-9-yl)phenyl)-9H-carbazole-3-carbonitrile (mCP-CN), CBP, 3,3'-bis(N-carbazolyl)-1,1'-biphenyl (mCBP), 1,3-Bis(carbazol-9-yl)benzene (mCP), Oxybis (2,1-phenylene))bis(diphenylphosphine oxide (DPEPO), 2,8-Bis(diphenylphosphoryl)dibenzothiophene (PPT), 1,3, 5-Tri[(3-pyridyl)-phen-3-yl]benzene (TmPyPB), 2,6-Di (9H-carbazol-9-yl)pyridine (PYD-2Cz), 2,8-di(9H-carbazol-9-yl)dibenzothiophene (DCzDBT), 3',5'-Di(carbazol-9-yl)-[1,1'-biphenyl]-3,5-dicarbonitrile (DCzTPA), 4'-(9H-carbazol-9-yl)biphenyl-3,5-dicarbonitrile (pCzB-2CN), 3'-(9H-carbazol-9-yl)biphenyl-3,5-dicarbonitrile (mCzB-2CN), Diphenyl-4-triphenylsilylphenyl-phosphine oxide (TPSO1), 9-(9-phenyl-9H-carbazol-6-yl)-9H-carbazole (CCP)), 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicarbazole.

Figure 3:
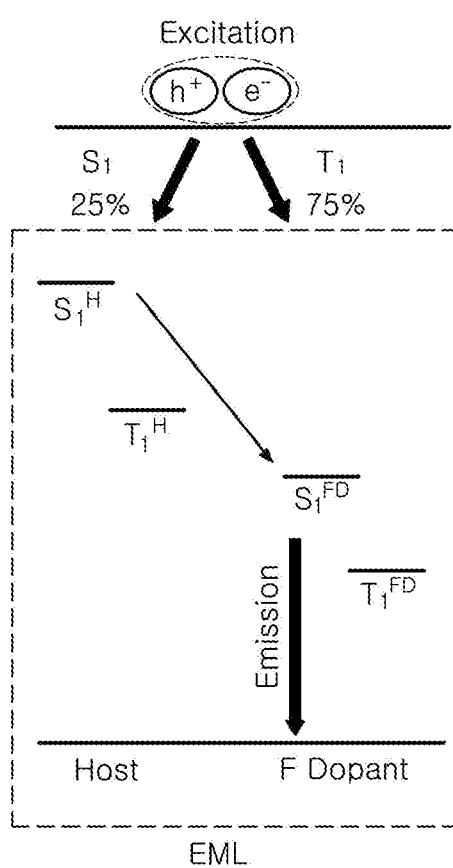
FIG. 3 is s schematic diagram illustrating luminous mechanism by energy level bandgap between a host and an organic compound as a fluorescent dopant in an EML in accordance with an exemplary embodiment of the present disclosure.

Particularly, each of an excited state singlet energy level $S_1^H$ and an excited state triplet energy level $T_1^H$ of the host may be higher than each of an excited state singlet energy level $S_1^{FD}$ and an excited state triplet energy level $T_1^{FD}$ of the first fluorescent dopant, respectively (See, FIG. 3).

The ETL 170 and the EIL 180 are laminated sequentially between the EML 160 and the second electrode 120. The ETL 170 includes a material having high electron mobility so as to provide electrons stably with the EML 160 by fast electron transportation.

In one exemplary embodiment, the ETL 170 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the likes.

For example, the ETL 170 may include, but is not limited to, tris-(8-hydroxyquinoline aluminum ($Alq_3$), 2-biphenyl-4-yl-5-(4-t-butylphenyl)-1,3,4-oxadiazole (PBD), spiro-PBD, lithium quinolate (Liq), 1,3,5-Tris(N-phenylbenzimidazol-2-yl)benzene (TPBi), Bis(2-methyl-8-quinolinolato-N1,O8)-(1,1'-biphenyl-4-olato)aluminum (BAlq), 4,7-diphenyl-1,10-phenanthroline (Bphen), 2,9-Bis (naphthalene-2-yl)4,7-diphenyl-1,10-phenanthroline (NBphen), 2,9-Dimethyl-4,7-diphenyl-1,10-phenathroline (BCP), 3-(4-Biphenyl)-4-phenyl-5-tert-butylphenyl-1,2,4-triazole (TAZ), 4-(Naphthalen-1-yl)-3,5-diphenyl-4H-1,2,4-triazole (NTAZ), 1,3,5-Tri(p-pyrid-3-yl-phenyl)benzene (TpPyPB), 2,4,6-Tris(3'-(pyridin-3-yl)biphenyl-3-yl) 1,3,5-triazine (TmPPPyTz), Poly[9,9-bis(3'-(N,N-dimethyl)-N-ethylammonium)-propyl)-2,7-fluorene]-alt-2,7-(9,9-dioctylfluorene)](PFNBr) and/or tris(phenylquinoxaline) (TPQ).

The EIL 180 is disposed between the second electrode 120 and the ETL 170, and can improve physical properties of the second electrode 120 and therefore, can enhance the life span of the OLED 100. In one exemplary embodiment, the EIL 180 may include, but is not limited to, an alkali halide such as LiF, CsF, NaF, $BaF_2$ and the likes, and/or an organic metal compound such as lithium benzoate, sodium stearate, and the likes.

In one exemplary embodiment, when the EML 160 includes the host and the organic compound represented by any of Chemical Formulae 1 to 2 as the first fluorescent dopant, it is necessary to adjust excited state singlet energy levels and/or excited state triplet energy levels between the host and the first fluorescent dopant. FIG. 3 is a schematic diagram illustrating a luminous mechanism by energy level bandgap between a host and a fluorescent dopant in a single-layered EML in accordance with an exemplary embodiment of the present disclosure.

As illustrated schematically in FIG. 3, each of the excited state singlet energy level $S_1^H$ and the excited state triplet energy level $T_1^H$ of the host is higher than each of the excited state singlet energy level $S_1^{FD}$ and the excited state triplet energy level $T_1^{FD}$ of the first fluorescent dopant, respectively, so that exciton energy generated in the host can be efficiently transferred to the fluorescent dopant. In one exemplary embodiment, an emission wavelength range of the host may overlap with an absorption wavelength range of the fluorescent dopant so that the exciton energy can be transferred much more efficiently from the first host to the first fluorescent dopant.

The EML 160 includes the organic compound represented by any of Chemical Formulae 1 to 2, which has a conformationally rigid naphtho fluoranthene core bonded by a hetero aromatic group at a sterically bent naphtho moiety in the naphtho fluoranthene core. The organic compound has narrow FWHM (full width at half maximum) so that the OLED 100 may have high color purity.

Figure 4:
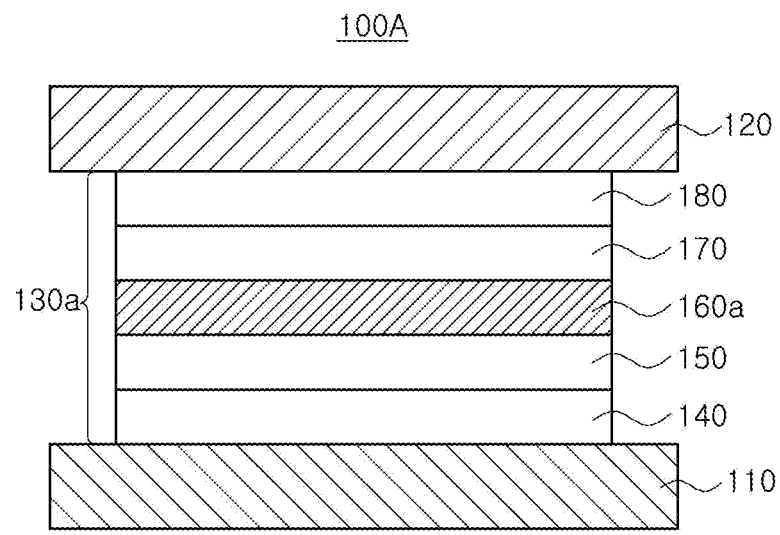
FIG. 4 is a schematic cross-sectional view illustrating an organic light-emitting diode in accordance with another exemplary embodiment of the present disclosure.

While the EML 160 includes only a host and a fluorescent dopant in the above embodiment, another EML may have two or more dopants. FIG. 4 is a schematic cross-sectional view illustrating an OLED in a single-layered EML in accordance with another exemplary embodiment of the present disclosure. As illustrated in FIG. 4, the OLED 100A in accordance with another embodiment of the present disclosure includes first and second electrodes 110 and 120 facing each other and an emission layer 130a disposed between the first and second electrodes 110, 120.

In one exemplary embodiment, the emission layer 130a may include an HIL 140, an HTL 150, an EML 160a, an ETL 170 and an EIL 180 each of which is laminated sequentially from the first electrode 110.

As described above, the first electrode 110 may be an anode and may include, but is not limited to, a conductive material having a relatively large work function values such as ITO, IZO, SnO, ZnO, ICO, AZO, and the likes. The second electrode 120 may be a cathode and may include, but is not limited to, a conductive material having a relatively small work function values such as Al, Mg, Ca, Ag, alloys or combination thereof.

The HIL 140 is disposed between the first electrode 110 and the HTL 150. The HIL 140 may include, but is not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 140 may be omitted in compliance with the structure of the OLED 100A.

The HTL 150 is disposed adjacently to the EML 160a between the first electrode 110 and the EML 160a. The HTL 150 may include, but is not limited to, aromatic amine compounds such as TPD, NPD(NPB), CBP, poly-TPD, TFB, TAPC), N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The ETL 170 is disposed between the EML 160a and the EIL 180. For example, the ETL 170 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the likes. For example, the ETL 170 may include, but is not limited to, $Alq_3$, PBD, spiro-PBD, Liq, TPBi, BAlq, Bphen, NBphen, BCP, TAZ, NTAZ, TpPyPB, TmPPPyTz, PFNBr and/or TPQ.

The EIL 180 is disposed between the second electrode 120 and the ETL 170. The ETL 180 may include, but is not limited to, an alkali halide such as LiF, CsF, NaF, $BaF_2$ and the likes, and/or an organic metal compound such as lithium benzoate, sodium stearate, and the likes.

In this embodiment, the EML 160a may include a host (a first host), a first dopant and a second dopant. The first dopant may be a delayed fluorescent dopant (T dopant) such as thermally activated delayed fluorescent dopant and the second dopant may be a fluorescent dopant (F dopant). For example, the organic compound represented by any of Chemical Formulae 1 to 2 may be used as the second dopant. When the EML 160a further includes the delayed fluorescent dopant as the first dopant, it is possible to implement OLED 100A that improve luminous efficiency remarkably by adjusting the energy levels among the host and the dopants.

An organic light emitting diode (OLED) emits light as holes injected from the anode and electrons injected from the cathode are combined to form excitons in an EML. Unstable excited state excitons return to a stable ground state. The external quantum efficiency (EQE; $\eta_{ext}$) of the luminous material applied into the EML can be calculated by the following Equation (1):

$$\eta_{ext} = \eta_{S/T} \times \Gamma \times \Phi \eta_{out\text{-}coupling} \quad (1)$$

In Equation (1), "$\eta_{S/T}$" is an exciton generation efficiency (singlet/triplet ratio); "r" is a charge balance factor; "$\Phi$" is a radiative quantum efficiency; "$\eta_{out\text{-}coupling}$" is an out-coupling efficiency.

"$\eta_{S/T}$" may also be understood as a transformation ratio from exciton to light (singlet/triplet ratio) and has a maximum value of 0.25 in case of fluorescent materials. Theoretically, when electrons meet holes to form exciton, a singlet exciton of a paired spin and a triplet exciton of an unpaired spin are produced by a ratio of 1:3 by spin arrangements. Only the singlet exciton among the excitons can be involved in emission processes in case of the fluorescent materials.

Charge balance factor "r" is a balance between holes and electrons both of which form excitons and generally has a value of "1" assuming 1:1 matching of 100%. "D" is a value related to a luminous efficiency of actual luminous materials and depends upon photoluminescence of dopant in a host-dopant system.

"$\eta_{out\text{-}coupling}$" is a ratio of light extracted outwardly among the emitted light in a luminous materials. When an isotropic luminous material is thermally deposited to form a thin film, each of luminous molecules does not have a specific orientation, but exists with random states. The out-coupling efficiency in such random orientation is generally assumed "0.2". Accordingly, when combining the 4 parameters of Equation (1) above, the OLED exhibits a luminous efficiency of 5% at maximum if a the prior art fluorescent material is used.

In contrast, phosphorescent materials use different luminous mechanism of converting both singlet excitons and triplet exciton into light. The phosphorescent materials can convert singlet excitons into triplet excitons through inter-system crossing (ISC). Therefore, it is possible to enhance luminous efficiency by applying the phosphorescent materials, which use both the singlet excitons and the triplet excitons during the luminous process, as an emission material compared to applying the fluorescent materials.

In case of using metal complexes having a heavy metal such as Ir, Pt, and the likes as the phosphorescent materials, it is possible to convert triplet state to singlet state through strong spin orbital coupling by the heavy metal. However, the prior art blue phosphorescent materials exhibit too low color purity for the display devices and exhibit very short luminous life span, and therefore, they have not been used in commercial display devices.

In this embodiment, the EML 160a includes the delayed fluorescent dopant as the first dopant so as to solve the problems accompanied by the conventional fluorescent materials and the phosphorescent materials. In an exemplary embodiment, the delayed fluorescent material is a thermally-activated delayed fluorescent (TADF) material.

Since the triplet excitons within the delayed fluorescent material can be activated by heat or an electrical field generated during driving the diode, the triplet excitons can be involved in emission processes. Since the delayed fluorescent material generally has both an electron donor moiety and an electron acceptor moiety, it can be converted to an intramolecular charge transfer (ICT) state. In case of using the delayed fluorescent material as a dopant, it is possible to use both the excitons of singlet energy level $S_1$ and the excitons of triplet energy level $T_1$ during the emission process.

Figure 5:
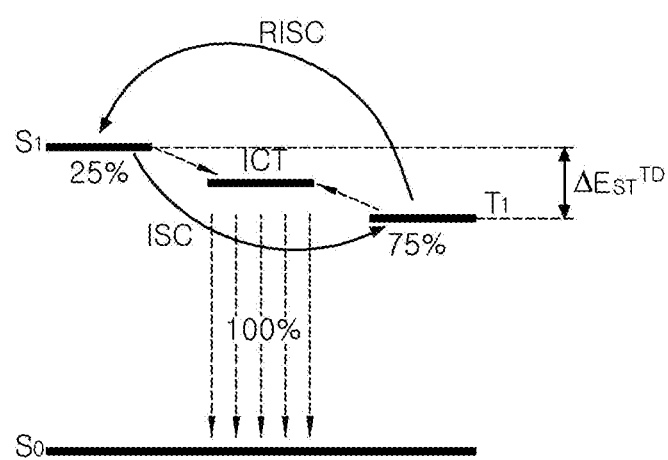
FIG. 5 is a schematic diagram illustrating luminous mechanism of the delayed fluorescent material in accordance with another exemplary embodiment of the present disclosure.

The luminous mechanism of the delayed fluorescent material will be explained. FIG. 5 is a schematic diagram illustrating luminous mechanism of the delayed fluorescent material in EML in accordance with another exemplary embodiment of the present disclosure. As illustrated in FIG. 5, the excitons of singlet energy level $S_1$ as well as the excitons of triplet energy level $T_1$ in the delayed fluorescent material can move to an intermediate energy level state, i.e. ICT state, and then the intermediate state excitons can be transferred to a ground state ($S_0$; $S_1 \rightarrow ICT \leftarrow T_1$). Since both the excitons of singlet energy level $S_1$ and the excitons of triplet energy level $T_1$ in the delayed fluorescent material are involved in the emission process, the delayed fluorescent material can improve luminous efficiency.

Since both the Highest Occupied Molecular Orbital (HOMO) and the Lowest Unoccupied Molecular orbital (LUMO) are widely distributed over the whole molecule within the common fluorescent material, it is not possible to inter-convert between the single energy level and the triplet energy level within it (selection rule). In contrast, since the delayed fluorescent material, which can be converted to ICT state, has little orbital overlaps between HOMO and LUMO, there is little interaction between the HOMO state molecular orbital and the LUMO state molecular orbital within the delayed fluorescent material. As a result, the changes of spin states of electrons does not have an influence on other electrons, and a new charge transfer band (CT band) that does not follow the selection rule is formed in the delayed fluorescent material.

In other words, since the delayed fluorescent material has the electron acceptor moiety spacing apart from the electron donor moiety within the molecule, a polarized state having a large dipole moment exists within the molecule. As the delayed fluorescent material having the polarized state of the dipole moment has little interaction between HOMO molecular orbital and LUMO molecular orbital, both the triplet energy level excitons and the singlet energy level excitons can be converted to ICT state. Accordingly, the excitons of triplet energy level $T_1$ as well as the excitons of singlet energy level $S_1$ can be involved in the emission process.

In case of driving a diode that includes the delayed fluorescent material, 25% excitons of singlet energy level $S_1$ and 75% excitons of triplet energy level $T_1$ are converted to ICT state by heat or electrical field, and then the converted excitons are transferred to the ground state $S_0$ with luminescence. Therefore, the delayed fluorescent material may have 100% internal quantum efficiency in theory.

The delayed fluorescent material must have an energy bandgap $\Delta E_{ST}^{TD}$ equal to or less than about 0.3 eV, for example, from about 0.05 to about 0.3 eV, between the singlet energy level $S_1$ and the triplet energy level $T_1$ so that exciton energy in both the singlet energy level and the triplet energy level can be transferred to the ICT state. The material having little energy level bandgap between the singlet energy level $S_1$ and the triplet energy level $T_1$ can exhibit common fluorescence with Inter system Crossing (ISC) in which the excitons of singlet energy level $S_1$ can be transferred to the excitons of triplet energy level $T_1$, as well as delayed fluorescence with Reverser Inter System Crossing (RISC) in which the excitons of triplet energy level $T_1$ can be transferred upwardly to the excitons of single energy level $S_1$, and then the exciton of singlet energy level $S_1$ transferred from the triplet energy level $T_1$ can be transferred to the ground state $S_0$.

Since the delayed fluorescent material can exhibit 100% internal quantum efficiency in theory, it can implement as high luminous efficiency as the conventional phosphorescent material including a heavy metal. However, the delayed fluorescent material has low luminous life span due to the use of the triplet energy as well as the singlet energy. Besides, due to the bond conformation between the electron acceptor and the electron donor and sterical twists within the delayed fluorescent material, and additional charge transfer transition (CT transition) caused thereby, the delayed fluorescent material shows an emission spectrum with a very broad FWHM in the course of emission, which results in poor color purity.

In this exemplary embodiment, it is possible to implement hyper-fluorescence by using the delayed fluorescent material as the first dopant so as to raise a generation ratio of the singlet exciton in the fluorescent material that can use only the singlet exciton energy. Since the delayed fluorescent material can utilize the triplet exciton energy as well as the singlet exciton energy, the fluorescent material can absorb the exciton energy emitted from the delayed fluorescent material, and therefore, the exciton energy absorbed by the fluorescent material can be utilized in the emission process with generating 100% singlet exciton.

In one exemplary embodiment of the present disclosure, the EML 160a includes the first host, a first dopant (delayed fluorescent dopant, TD) and the organic compound represented by any of Chemical Formulae 1 to 2 as the second dopant (fluorescent dopant, FD) so as to prevent the color purity of the OLED 100A from being lowered in spite of using the delayed fluorescent material as the first dopant. In this case, it is important to adjust energy levels among the host and the dopants to transfer exciton energy from the host to the second dopant through the first dopant.

Figure 6:
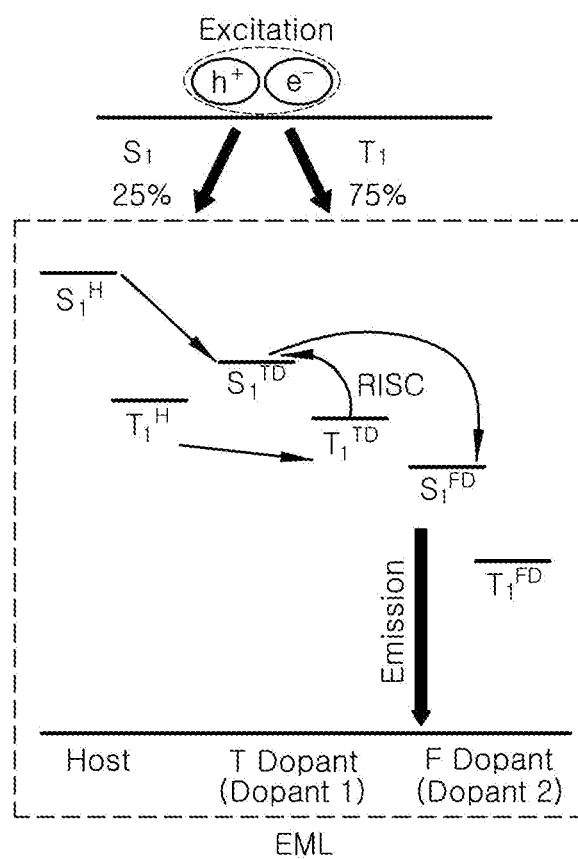
FIG. 6 is a schematic diagram illustrating luminous mechanism by energy level bandgap among a host, a fluorescent dopant and a delayed fluorescent dopant in an EML in accordance with another exemplary embodiment of the present disclosure.

FIG. 6 is a schematic diagram illustrating a luminous mechanism by energy level bandgap among the host, the first dopant (delayed fluorescent dopant) and the second dopant (fluorescent dopant) in a single-layered EML in accordance with another exemplary embodiment of the present disclosure. As illustrated in FIG. 6, each of an excited state singlet energy level $S_1^H$ and an excited state triplet energy $T_1^H$ of the host must be higher than each of an excited state singlet energy level $S_1^{TD}$ and an excited state triplet energy level $T_1^{TD}$ of the delayed fluorescent dopant, respectively, so that the exciton energy generated in the host can be transferred to the delayed fluorescent dopant in advance.

When the excited state triplet energy level $T_1^H$ of the host is not higher enough than the excited state triplet energy level $T_1^{TD}$ of the delayed fluorescent dopant, the excitons of the triplet state level $T_1^{TD}$ of the delayed fluorescent dopant can be reversely transferred to the excited state triplet energy level $T_1^H$ of the host. Accordingly, the excitons of the triplet state level $T_1^{TD}$ of the delayed fluorescent dopant may be quenched as a non-emission and they cannot be involved in the emission. For example, the excited state triplet energy level $T_1^H$ of the host may be high by at least 0.2 eV compared to the excited state triplet energy level $T_1^{TD}$ of the first dopant.

Also, the delayed fluorescent dopant (first dopant) must have the energy bandgap ($\Delta_{ES}^{TD}$) between the singlet energy level $S_1^{TD}$ and the triplet energy level $T_1^{TD}$ of at most 0.3 eV (See, FIG. 5). In contrast, the energy bandgap both of the singlet energy level $S_1^H$ and the triplet energy level $T_1^H$ of the host, and the singlet energy level $S_1^{FD}$ and the triplet energy level $T_1^{FD}$ of the fluorescent dopant (second dopant) may be above about 0.3 eV.

When the energy bandgaps between the singlet energy levels $S_1^H$ and $S_1^{FD}$ and the triplet energy levels $T_1^H$ and $T_1^{FD}$ of the host and the second dopant are equal to or less than about 0.3 eV, RISC and ISC luminous mechanisms by the host and the second dopant may decrease the luminous life span of the OLED 100A. For example, the energy bandgap between the singlet energy level $S_1^H$ and the triplet energy level $T_1^H$ of the host and the energy bandgap between the singlet energy level $S_1^{FD}$ and the triplet energy level $T_1^{FD}$ of the second dopant may be, but are not limited to, more than about 0.3 eV and equal to or less than about 1.5 eV.

Besides, it is necessary to adjust the Highest Occupied Molecular Orbital (HOMO) energy levels and the Lowest Unoccupied Molecular Orbital (LUMO) energy levels of the host and the delayed fluorescent dopant properly. For example, it is preferable that an energy level bandgap ($|HOMO^H-HOMO^{TD}|$) between a Highest Occupied Molecular Orbital energy level ($HOMO^{TD}$) of the host and a Highest Occupied Molecular Orbital energy level (HOMOm) of the delayed fluorescent dopant, or an energy level bandgap ($|LUMO^H-LUMO^{TD}|$) between a Lowest Unoccupied Molecular Orbital energy level ($LUMO^H$) of the host and a Lowest Unoccupied Molecular Orbital energy level ($LUMO^{TD}$) of the first dopant may be equal to or less than about 0.5 eV, for example, between about 0.1 eV to about 0.5 eV. In this case, the charges can be moved efficiently from the host to the delayed fluorescent dopant and thereby the ultimate luminous efficiency may be enhanced.

In addition, it is necessary to implement OLED that enables transfer energies from the delayed fluorescent dopant, which has been converted to ICT complex state by RISC, to the fluorescent dopant in the EML 160a, and that has high luminous efficiency and color purity. In order to implement such an OLED, each of the excited state singlet energy level $S_1^{TD}$ and the excited state triplet energy level $T_1^{TD}$ of the first dopant is higher than each of an excited state singlet energy level $S_1^{FD}$ and an excited state triplet energy level $T_1^{FD}$ of the second dopant, respectively.

Particularly, it is very important to efficiently transfer exciton energy from the delayed fluorescent material to the fluorescent material in order to enhance luminous efficiency of an OLED in which the fluorescent material is emitted ultimately for implementing hyper-fluorescence. The most important factor for determining the energy transfer efficiency from the delayed fluorescent material to the fluorescent material is an overlap between an emission wavelength range of the delayed fluorescent material and an absorption wavelength range of the fluorescent material which receives the exciton energy from the delayed fluorescent material.

The blue emitting delayed fluorescent material may have typical emission wavelength of maximum photoluminescence (PL $\lambda_{max}$) of about 470 nm, at least about 450 nm. Accordingly, blue fluorescent material must have a wavelength of maximum absorption (Abs. $\lambda_{max}$) of at least 440 nm so that it can receive the exciton energy efficiently from the blue emitting delayed fluorescent material. Besides, the ultimately emitting fluorescent material in the hyper-fluorescence mechanism must have PL $\lambda_{max}$ of about 460 nm so as to implement deep blue luminescence.

Figure 7:
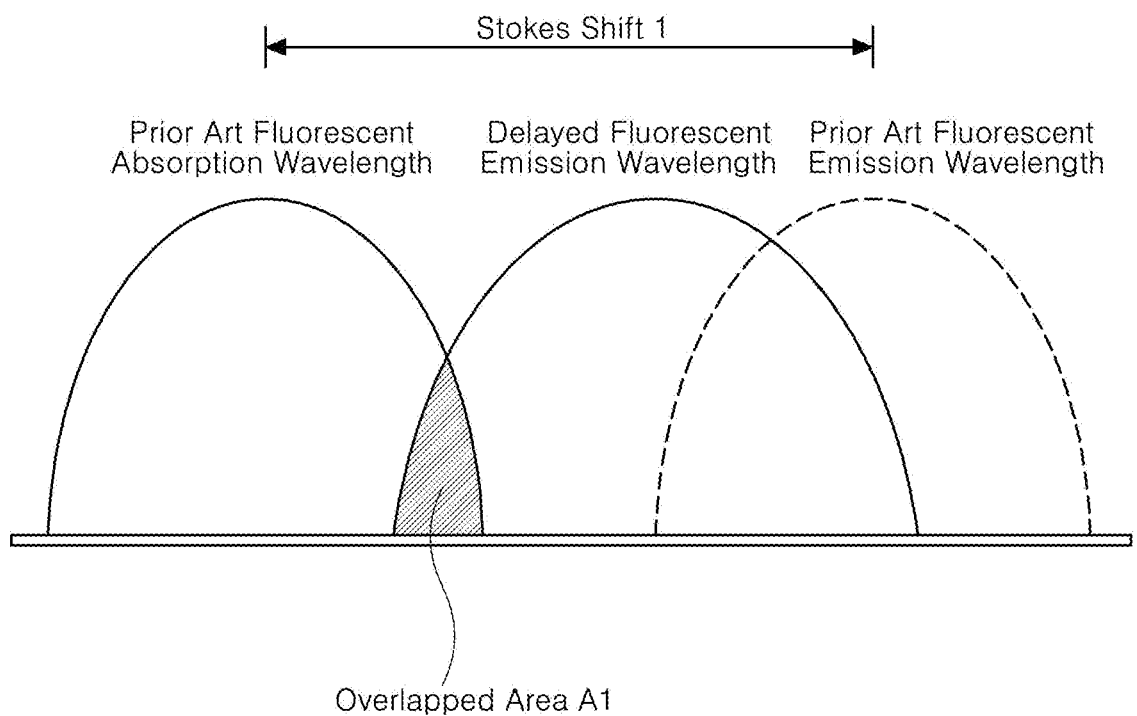
FIG. 7 is a schematic diagram illustrating relationships among absorption and emission wavelengths in case an exciton energy is transferred from the delayed fluorescent material to the fluorescent material in accordance with the prior art.

However, as illustrated in FIG. 7, which is a schematic diagram illustrating relationships among absorption and emission wavelength ranges in case an exciton energy is transferred from the delayed fluorescent material to a prior art fluorescent material, the prior art blue fluorescent material may have PL $\lambda_{max}$ of about 460 nm, while it has short Abs. $\lambda_{max}$ less than 435 nm. In other words, the prior art blue fluorescent material has very broad Stokes Shift "Stokes Shift 1", which is defined as a difference between the PL $\lambda_{max}$ and the Abs. $\lambda_{max}$. Since there exists a very small overlap area "Overlapped Area A1" between the absorption wavelength range of the prior art fluorescent material and the emission wavelength range of the delayed fluorescent material, the exciton energy is transferred only poorly from the delayed fluorescent material to the prior art fluorescent material.

Figure 8:
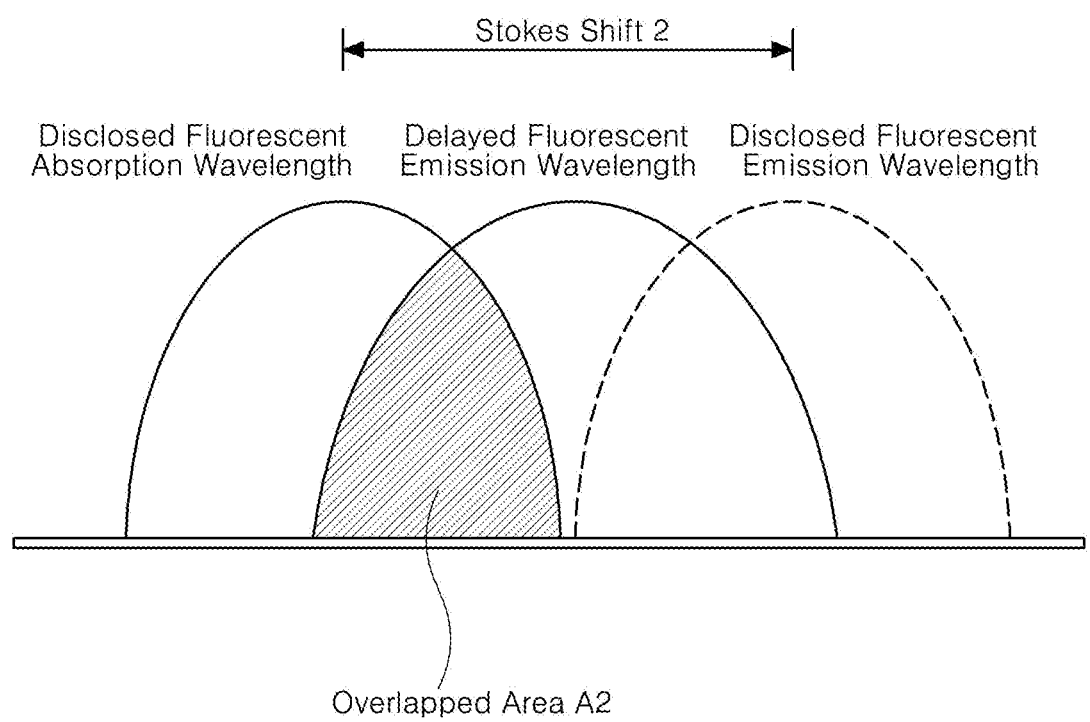
FIG. 8 is a schematic diagram illustrating relationships among absorption and emission wavelengths in case an exciton energy is transferred from the delayed fluorescent material to the fluorescent material in accordance with another exemplary embodiment of the present disclosure.

In contrast, as illustrated in FIG. 8, which a schematic diagram illustrating relationships among absorption and emission wavelength ranges in case an exciton energy is transferred from the delayed fluorescent material to the fluorescent material in accordance with another exemplary embodiment of the present disclosure, the organic compound represented by any of Chemical Formulae 1 to 2 may have PL $\lambda_{max}$ of similar to the PL $\lambda_{max}$ of the prior art fluorescent material, while it has Abs. $\lambda_{max}$ of more than or equal to 440 nm, which is longer compared to the Abs. $\lambda_{max}$ of the prior art fluorescent material. In other words, the organic compound represented by any of Chemical Formulae 1 to 2 has Stokes Shift "Stokes Shift 2" less than about 20 nm, which is much smaller than the "Stokes Shift 1" of the prior art fluorescent material (Stokes Shift 2<Stokes Shift 1). Accordingly, there exists a very broad or large overlap area "Overlapped Area A2" between the absorption wavelength range of the organic compound represented by any of Chemical Formulae 1 to 2 and the emission wavelength range of the delayed fluorescent material (Overlapped Area A2>Overlapped Area A1). As a result, the exciton energy can be efficiently transferred from the delayed fluorescent material to the organic compound fluorescent material so that OLED 100A can enhance the luminous efficiency.

In contrast, in case a compound includes a hetero aromatic group, for adjusting a color sensitivity of the compound, bonded to other positions, for example, such as the position bonded by $R_1$ to $R_3$ defined in Chemical Formula 1, of the naphtho fluoranthene core, such a compound has large or broad Stokes Shift as its Abs. $\lambda_{max}$ is moved toward shorter wavelength ranges. Accordingly, the exciton energy cannot be transferred efficiently from the delayed fluorescent material to the compound, as there is a small overlap area between an absorption wavelength range of the compound and an emission wavelength range of the delayed fluorescent material.

Besides, in case a compound includes a homo aromatic group bonded to a position adjacently to the sterically bent naphtho moiety of the naphtho fluoranthene core, for example a position bonded by X defined in Chemical Formula 1, such a compound does not have any group for adjusting color sensitivity of the compound, while its Stokes Shift may be reduced. Accordingly, it is not possible to implement blue emission having high color purity as the PL $\lambda_{max}$ and Abs. $\lambda_{max}$ of the compound are generally biased toward shorter wavelengths.

Accordingly, the OLED 100A can implement hyperfluorescence having high luminous efficiency, color purity and luminous life span as well as low consumption power by using the organic compound represented by any of Chemical Formulae 1 to 2, which includes a conformationally rigid naphtho fluoranthene core and a hetero aromatic group, with regard to color sensitivity, bonded to a specific position adjacent to the sterically bent naphtho moiety, as the fluorescent dopant The excitons of triplet energy level $T_1$ can be transferred to the excitons of the singlet energy level $S_1$ in the delayed fluorescent dopant by RISC, and the singlet energy of the delayed fluorescent dopant can be transferred to the fluorescent dopant in the same EML by Dexter energy transfer that depends upon wave function overlaps among adjacent molecules by inter-molecular electron exchanges and exciton diffusions.

In this case, the ultimate emission in the EML 160a is done at the second dopant, i.e., the organic compound represented by any of Chemical Formulae 1 to 2, which has a narrow FWHM (full width at half maximum) during transferring the exciton energy from the excited state to the ground state. The OLED 100A can enhance its color purity. Besides, since the OLED 100A can extremely improve the luminous efficiency, it is possible to obtain a hyper-fluorescent diode.

As such, when the EML 160a includes a host (first host), a delayed fluorescent dopant (first dopant) and the organic compound represented by any of Chemical Formulae 1 to 2 as a fluorescent dopant (second dopant), it is possible to implement hyper fluorescence and to improve color purity by adjusting energy levels among the host, the first dopant and the second dopant. The excitons of triplet energy level $T_1$ can be transferred to the excitons of the singlet energy level $S_1$ in the delayed fluorescent dopant by RISC, and the singlet energy of the delayed fluorescent dopant can be transferred to the fluorescent dopant in the same EML by Dexter energy transfer mechanism, which depends upon wave function overlaps among adjacent molecules by inter-molecular electron exchanges and exciton diffusions.

In one exemplary embodiment, the host in the EML 160a may include, but is not limited to, mCP-CN, CBP, mCBP, mCP, DPEPO, TmPyPB, PYD-2Cz, DCzDBT, DCzTPA, pCzB-2CN, mCzB-2CN, TPSO1, CCP, 4-(3-(triphenylen-2-yl)phenyl)dibenzo[b,d]thiophene, 9-(4-(9H-carbazol-9-yl) phenyl)-9H-3,9'-bicarbazole, 9-(3-(9H-carbazol-9-yl)phenyl)-9H-3,9'-bicarbazole and/or 9-(6-(9H-carbazol-9-yl) pyridin-3-yl)-9H-3,9'-bicarbazole.

In another exemplary embodiment, the first dopant (delayed fluorescent dopant) used in the EML 160a may include, but is not limited to, bis(4-(9H-carbazol-9-yl)phenyl)methanone (Cz2BP), 9-(3-(9H-Carbazol-9-yl)-5-(4,6-diphenyl-1,3,5-triazin-2-yl)phenyl)-9H-carbazole (DcrTrZ), 3-(9H-Carbazol-9-yl)-9-(4-(4,6-diphenyl-1,3,5-triazin-2-yl) phenyl)-9H-carbazole (4-DcrTrZ), 10-(4-(4,6-diphenyl-1,3, 5-triazin-2-yl)phenyl)-10H-spiro[acridine-9,9'-xanthene], 4,5-di(9H-carbazol-9-yl) phthalonitrile (2CzPN), 2,4,5,6-Tetra(9H-carbazol-9-yl)isophthalonitile (4CzIPN), 3,4,5,6-Tetrakis(carbazol-9-yl)-1,2-dicyanobenzene (4CzPN), 4,4"-Di(10H-phenoxazin-10-yl)-[1,1:2,1-terphenyl]-4,5-dicarbonitrile (Px-VPN), 9,9',9"-(5-(4,6-diphenyl-1,3,5-triazin-2-yl)benzene-1,2,3-triyl) tris(9H-carbazole (TczTRZ) and/or 12-(4-(4,6-diphenyl-1,3,5-triazin-2-yl) phenyl-5-phenyl-5,12-dihydroindolo[3,2-a]carbazole (32al-CTRZ).

When the EML 160a includes the host, the delayed fluorescent dopant (first dopant) and the fluorescent dopant (second dopant), the first and second dopants may be comprised in about 1 to about 50% by weight in the EML 160a.

As described above, since the organic compound represented by any of Chemical Formulae 1 to 2 includes a hetero aromatic group bonded to the sterically bent naphtho moiety, its Stokes Shift becomes smaller, as its PL $\lambda_{max}$ Abs. $\lambda_{max}$ are moved toward longer wavelength range. Accordingly, the OLED 100A can enhance its luminous efficiency and implement hyper-fluorescence, as the overlap area between the absorption wavelength range of the organic compound and the emission wavelength range of the delayed fluorescent dopant is large and exciton energy is efficiently transferred from the delayed fluorescent dopant to the fluorescent dopant. Besides, since the ultimate emission is done in the organic compound represented by any of Chemical Formulae 1 to 2, which has narrow FWHM, as the exciton energy is dropped from the excited state to the ground state, the OLED 100A can improve its color purity and luminous life span. Besides, since the EML 160a includes the delayed fluorescent material as the first dopant, the OLED 100A can maximize its luminous efficiency.

When the EML 160a includes the host, the delayed fluorescent dopant (first dopant) and the fluorescent dopant (second dopant), it may comprise the host in a higher weight ratio than the dopants. In one embodiment, the EML 160a may comprise the first dopant in a higher weight ratio than the second dopant. For example, the weight content of the host may be larger than the weight content of the first dopant in the EML 160a, and the weight content of the first dopant may be larger than the weight content of the second dopant in the EML 160a. In this case, the exciton energy can be efficiently transferred from the first dopant to the second dopant in the EML 160a. For example, when the EML 160a includes the host, the delayed fluorescent dopant (first dopant) and the fluorescent dopant (second dopant), the first and second dopants may be comprised in about 1 to about 50% by weight in the EML 160a.

Figure 9:
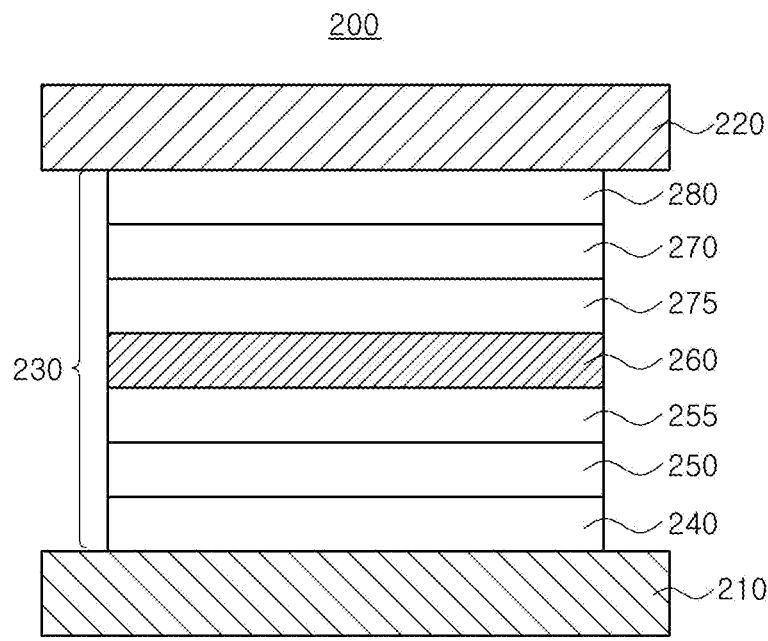
FIG. 9 is a schematic cross-sectional view illustrating an organic light-emitting diode in accordance with another exemplary embodiment of the present disclosure.

In addition, an OLED in accordance with the present disclosure may further comprise one or more exciton blocking layers. FIG. 9 is a schematic cross-sectional view illustrating an organic light-emitting diode in accordance with another exemplary embodiment of the present disclosure. As illustrated in FIG. 9, an OLED 200 in accordance with the third embodiment of the present disclosure includes first and second electrodes 210 and 220, and an emission layer 230 disposed between the first and second electrodes 210 and 220.

In an exemplary embodiment, the emission layer 230 includes an HIL 240, an HTL 250, an EML 260, an ETL 270 and an EIL 280 each of which is laminated sequentially above the first electrode 210. Besides, the emission layer 230 further includes a first exciton blocking layer, i.e. an electron blocking layer (EBL) 255 disposed between the HTL 250 and the EML 260 and/or a second exciton blocking layer, i.e., a hole blocking layer (HBL) 275 disposed between the EML 260 and the ETL 270.

As described above, the first electrode 210 may be an anode and may include, but is not limited to, a conductive material having a relatively large work function values such as ITO, IZO, SnO, ZnO, ICO, AZO, and the likes. The second electrode 220 may be a cathode and may include, but is not limited to, a conductive material having a relatively small work function values such as Al, Mg, Ca, Ag, alloy thereof or combination thereof.

The HIL 240 is disposed between the first electrode 210 and the HTL 250. The HIL 240 may include, but is not limited to, MTDATA, NATA, 1T-NATA, 2T-NATA, CuPc, TCTA, NPB(NPD), HAT-CN, TDAPB, PEDOT/PSS and/or N-(biphenyl-4-yl)-9,9-dimethyl-N-(4-(9-phenyl-9H-carbazol-3-yl)phenyl)-9H-fluoren-2-amine. The HIL 240 may be omitted in compliance with the structure of the OLED 200.

The HTL 250 is disposed adjacently to the EML 260 between the first electrode 210 and the EML 260. The HTL 250 may include, but is not limited to, aromatic amine compounds such as TPD, NPD(NPB), CBP, poly-TPD, TFB, TAPC, N-(biphenyl-4-yl)-9,9-dimethyl-N-(4-(9-phenyl-9H-carbazol-3-yl)phenyl)-9H-fluoren-2-amine and/or N-(biphenyl-4-yl)-N-(4-(9-phenyl-9H-carbazol-3-yl)phenyl)biphenyl-4-amine.

The EML 260 may include a host (first host) and at least one dopant. In an exemplary embodiment, the EML 260 may comprise a host and the organic compound represented by any of Chemical Formulae 1 to 2 as a fluorescent dopant (first fluorescent dopant). For example, the EML 260 may comprise the fluorescent dopant in about 1% to 50% by weight. In an exemplary embodiment, each of the excited state triplet energy level $T_1^H$ and the excited state singlet energy level $S_1^H$ of the host is higher than each of the excited state triplet energy level $T_1^{FD}$ and the excited state singlet energy level $S_1^{FD}$ of the first fluorescent dopant, respectively (See, FIG. 3).

In another exemplary embodiment, the EML 260 may include a host (first host), a first dopant and a second dopant. The first dopant may be a delayed fluorescent dopant, and the second dopant may be a fluorescent dopant. The organic compound represented by any of Chemical Formulae 1 to 2 may be used as the second dopant.

In one exemplary embodiment, the host may include, but is not limited to, pCzB-2CN, mCzB-2CN, TPSO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicarbazole. In another embodiment, the first dopant may include, but is not limited to, Cz2BP, DcrTrZ, 4-DcrTrZ, 10-(4-(4,6-diphenyl-1,3,5-triazin-2-yl)phenyl)-10H-spiro[acridine-9,9'-xanthene], 2CzPN, 4CzIPN, 4CzPN, Px-VPN, TczTRZ and/or 32alC-TRZ).

In this case, an energy bandgap between the excited state singlet energy level $S_1^{TD}$ and the excited state triplet energy level $T_1^{TD}$ of the first dopant may be equal to or less than about 0.3 eV. In addition, each of the excited state singlet energy level $S_1^H$ and the excited state triplet energy level $T_1^H$ of the host are higher than each of the excited state singlet energy level $S_1^{TD}$ and/or the excited state triplet energy level $T_1^{TD}$ of the first dopant, respectively. For example, the excited state triplet energy level $T_1^H$ of the host may be higher than the excited state triplet energy level $T_1^{TD}$ of the first dopant by at least about 0.2 eV. Besides, each of the excited state singlet energy level $S_1^{TD}$ and the excited state triplet energy level $T_1^{TD}$ of the first dopant is higher than each of the excited state singlet energy level $S_1F$ and the excited state triplet energy level $T_1^{FD}$ of the second dopant, respectively.

Also, an energy level bandgap ($|HOMO^H-HOMO^{TD}|$) between a Highest Occupied Molecular Orbital energy level ($HOMO^H$) of the host and a Highest Occupied Molecular Orbital energy level ($HOMO^{TD}$) of the first dopant, or an energy level bandgap ($|LUMO^H-LUMO^{TD}|$) between a Lowest Unoccupied Molecular Orbital energy level (LUMO$^H$) of the host and a Lowest Unoccupied Molecular Orbital energy level (LUMO$^{TD}$) of the first dopant may be equal to or less than about 0.5 eV. In case the EML 260 includes the host, the first dopant and the second dopant, the EML 260 may comprise the first and second dopants in about 1 to about 50% by weight.

The ETL 270 is disposed between the EML 260 and the EIL 280. For example, the ETL 270 may include, but is not limited to, oxadiazole-based compounds, triazole-based compounds, phenanthroline-based compounds, benzoxazole-based compounds, benzothiazole-based compounds, benzimidazole-based compounds, triazine-based compounds, and the likes. For example, the ETL 270 may include, but is not limited to, Alq$_3$, PBD, spiro-PBD, Liq, TPBi, BAlq, Bphen, NBphen, BCP, TAZ, NTAZ, TpPyPB, TmPPPyTz, PFNBr and/or TPQ.

The EL 280 is disposed between the second electrode 220 and the ETL 270. The EIL 280 may include, but is not limited to, an alkali halide such as LiF, CsF, NaF, BaF$_2$ and the likes, and/or an organic metal compound such as lithium benzoate, sodium stearate, and the likes.

When holes are transferred to the second electrode 220 via the EML 260 and/or electrons are transferred to the first electrode 210 via the EML 260, the OLED 200 may have short life span and reduced luminous efficiency. In order to prevent these phenomena, the OLED 200 in accordance with the third embodiment of the present disclosure has at least one exciton blocking layer adjacent to the EML 260.

For example, the OLED 200 of the exemplary embodiment includes the EBL 255 between the HTL 250 and the EML 260 so as to control and prevent electron transfers. In one exemplary embodiment, the EBL 255 may include, but is not limited to, TCTA, Tris[4-(diethylamino)phenyl] amine, N-(biphenyl-4-yl)-9,9-dimethyl-N-(4-(9-phenyl-9H-carbazol-3-yl)phenyl)-9H-fluorene-2-amine, TAPC, MTDATA, mCP, mCBP, CuPc, N,N'-bis[4-(bis(3-methylphenyl)amino)phenyl]-N,N'-diphenyl-[1,1'-biphenyl]-4,4'-diamine (DNTPD) and/or TDAPB.

In addition, the OLED 200 may further include the HBL 275 as a second exciton blocking layer between the EML 260 and the ETL 270 so that holes cannot be transferred from the EML 260 to the ETL 270. In one exemplary embodiment, the HBL 275 may include, but is not limited to, oxadiazole-based compounds, triazole-based compounds, phenanthroline-based compounds, benzoxazole-based compounds, benzothiazole-based compounds, benzimidazole-based compounds, and triazine-based compounds.

For example, the HBL 275 may include a compound having a relatively low HOMO energy level compared to the emitting material in EML 260. The HBL 275 may include, but is not limited to, BCP, BAlq, Alq$_3$, PBD, spiro-PBD, Liq, Bis-4,5-(3,5-di-3-pyridylphenyl)-2-methylpyrimidine (B3PYMPM) and combination thereof.

The OLED 200 in accordance with the third embodiment of the present disclosure includes the organic compound represented by any of Chemical Formulae 1 to 2 as the dopant in the EML 260. It is possible to manufacture the OLED 200 in such a way that it can be driven at lower driving voltage and that its luminous efficiency and color purity are enhanced. Besides, when the EML 260 includes the delayed fluorescent dopant, it is possible to extremely improve the luminous efficiency (hyper-fluorescence) and the life span of the OLED 200. Beside, the OLED 200 further includes at least one exciton blocking layers 255 and 275. Since such exciton blocking layers 255 and 275 can prevent emissions at interfaces between the charge transport layers 250 and 270 and the EML 260, the OLED 200 has a further enhanced luminous efficiency and life span.

Figure 10:
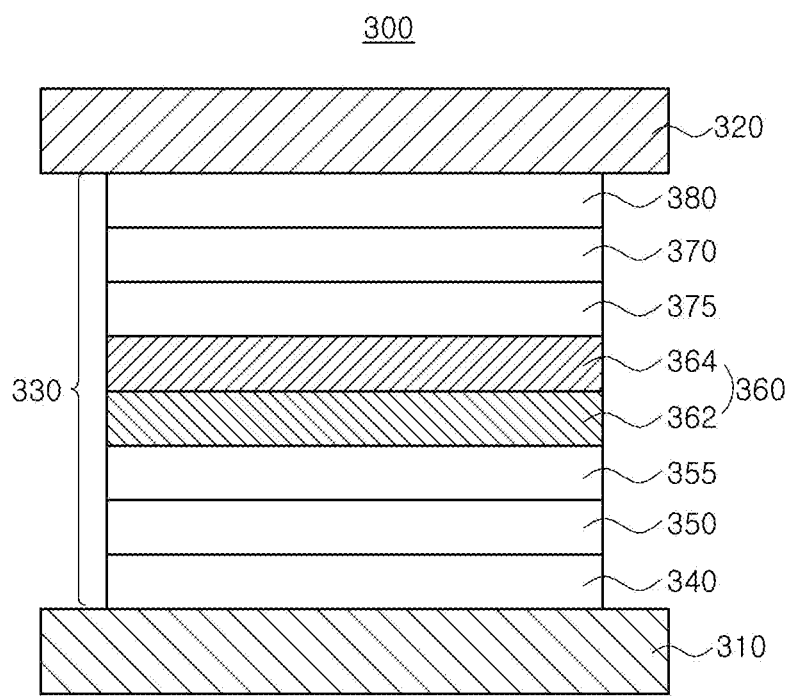
FIG. 10 is a schematic cross-sectional view illustrating an organic light-emitting diode n accordance with another exemplary embodiment of the present disclosure.

The OLEDs in accordance with the previous embodiments have only single-layered emitting material layer. Alternatively, an OLED in accordance with the present disclosure may include multiple-layered emitting material layer. FIG. 10 is a schematic cross-sectional view illustrating an organic light-emitting diode including a double-layered EML in accordance with another exemplary embodiment of the present disclosure.

As illustrated in FIG. 10, the OLED 300 in accordance with an exemplary fourth embodiment of the present disclosure includes first and second electrodes 310 and 320 facing each other and an emission layer 330 disposed between the first and second electrodes 310 and 320.

In one exemplary embodiment, the emission layer 330 includes an HIL 340, an HTL 350, and EML 360, an ETL 370 and an EIL 380 each of which is laminated sequentially over the first electrode 310. Beside, the emission layer 330 may include an EBL 355 as a first exciton blocking layer disposed between the HTL 350 and the EML 360, and/or an HBL 375 as a second exciton blocking layer disposed between the EML 360 and the ETL 370.

In this embodiment, the EML 360 includes a first EML (EML1) 362 disposed between the EBL 355 and the HBL 375 and a second EML (EML2) 364 disposed between the EML1 362 and the HBL 375. One of the EML1 362 and the EML2 364 includes the organic compound represented by any of Chemical Formulae 1 to 2 as a fluorescent dopant (first fluorescent dopant, F dopant), and the other of the EML1 362 and the EML2 364 includes a delayed fluorescent dopant (T dopant). Hereinafter, the EML 360, where the EML1 362 includes the fluorescent dopant and the EML2 364 includes the delayed fluorescent dopant, will be explained.

The EML1 362 may include a first host and a first fluorescent dopant that is the organic compound represented by any of Chemical Formulae 1 to 2. While the organic compound represented by any of Chemical Formulae 1 to 2 has a narrow FWHM and therefore, and can enhance its color purity, its luminous efficiency is limited because its triplet excitons cannot be involved in the emission process.

In contrast, the EML2 364 may include a second host and the delayed fluorescent dopant. The delayed fluorescent dopant in the EML2 364 has little energy bandgap between the excited state triplet energy level $T_1^{TD}$ and the excited state singlet energy level $S_1^{TD}$, i.e. equal to or less than about 0.5 eV, and its exited state triplet energy can be transferred to its excited state singlet energy by RISC. While the delayed fluorescent dopant has high quantum efficiency, it shows poor color purity due to its wide FWHM.

However, in this exemplary embodiment, both the singlet energy and the triplet energy of the delayed fluorescent dopant in EML2 364 can be transferred to the first fluorescent dopant comprised in the EML1 362 disposed adjacently to the EML2 364 by FRET (Forster resonance energy transfer) that transfers energy non-radiatively through electrical fields by dipole-dipole interactions. Accordingly, the ultimate emission is done at the first fluorescent dopant in the EML1 362.

Figure 11:
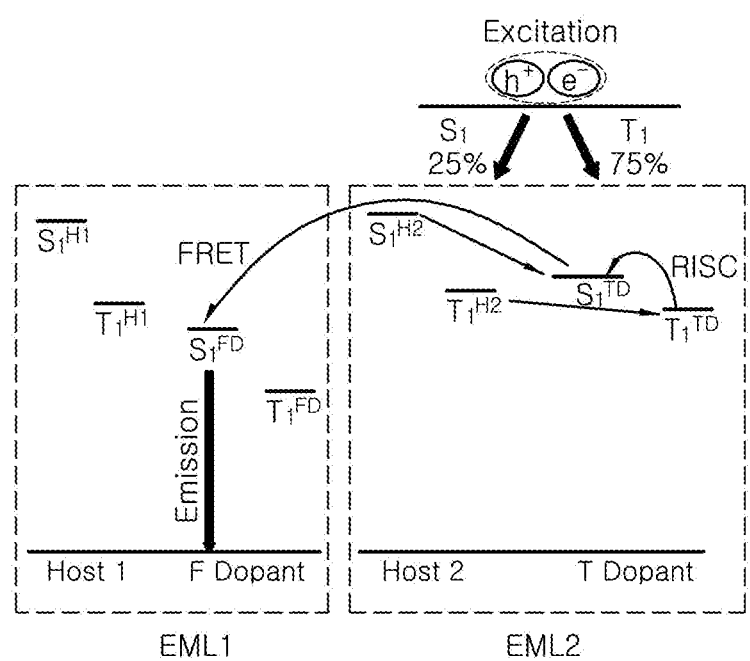
FIG. 11 is a schematic diagram illustrating luminous mechanism by energy level bandgap among a host, a delayed fluorescent dopant and a fluorescent material in an EML in accordance with another exemplary embodiment of the present disclosure.

In other words, the triplet energy of the delayed fluorescent dopant is converted to the singlet energy of the delayed fluorescent dopant in the EML2 364 by RISC, and the singlet energy of the delayed fluorescent dopant is transferred to the singlet energy of the first fluorescent dopant because the excited state singlet energy level $S_1^{TD}$ of the delayed fluorescent dopant is higher than the excited state singlet energy level $S_1^{FD}$ of the first fluorescent dopant (See, FIG. 11). The first fluorescent dopant in the EML1 362 can emit light in a twofold manner, namely by using the singlet energy and the triplet energy. Particularly, the organic compound as the first fluorescent dopant in the EML1 362 has very narrow Stokes Shift (See, FIG. 8) and can emit blue light with high color purity. Therefore, the OLED 300 can show hyper-fluorescence caused by an efficient energy transfer from the delayed fluorescent material in the EML2 364 to the fluorescent dopant in the EML1 362.

In this case, the delayed fluorescent dopant only acts as transferring energy to the first fluorescent dopant. The EML2 364 including the delayed fluorescent dopant is not involved in the ultimate emission process, while the EML1 362 including the first fluorescent dopant emits light.

Each of the EML1 362 and the EML2 364 includes the first host and the second host, respectively. For example, each of the first host and the second host may respectively include, but is not limited to, mCP-CN, CBP, mCBP, MCP, DPEPO, PPT, TmPyPB, PYD-2CZ, DCzDBT, DCzTPA, pCzB-2CN, mCzB-2CN, TPSO1, CCP, 4-(3-(triphenylen-2-yl)phenyl)dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicarbazole.

Besides, the delayed fluorescent dopant, which can be included in the EML2 364, may include, but is not limited to, Cz2BP, DcrTrZ, 4-DcrTrZ, 10-(4-(4,6-diphenyl-1,3,5-triazin-2-yl)phenyl)-10H-spiro[acridine-9,9'-xanthene], 2CzPN, 4CzIPN, 4CzPN, Px-VPN, TczTRZ and/or 32alC-TRZ.

In one exemplary embodiment, each of the first and second hosts may be contained in a higher weight ratio than the first fluorescent dopant and the delayed fluorescent dopant in the EML1 362 and the EML2 364, respectively. Besides, the weight ratio of the delayed fluorescent dopant in the EML2 364 may be higher than the weight ratio of the first fluorescent dopant in the EML1 362. In this case, it is possible to transfer enough energy from the delayed fluorescent dopant in the EML2 364 to the first fluorescent dopant in the EML1 362.

Energy level relationships among the materials in the EML 360 including two EMLs 362 and 364 will be explained. FIG. 11 is a schematic diagram illustrating luminous mechanism by energy level bandgap among a host, a delayed fluorescent dopant and a fluorescent material in a double-layered EML in accordance with another exemplary embodiment of the present disclosure. As illustrated in FIG. 11, each of an excited state singlet energy level $S_1^{H1}$ and an excited state triplet energy level $T_1^{H1}$ of the first host is higher than each of an excited state singlet energy level $S_1^{FD}$ and an excited state triplet energy level $T_1^{FD}$ of the fluorescent dopant in the EML 1 362, respectively.

Also, each of an excited state singlet energy level $S_1^{H2}$ and an excited state triplet energy level $T_1^{H2}$ of the second host is higher than each of an excited state singlet energy level $S_1^{TD}$ and an excited state triplet energy level $T_1^{TD}$ of the delayed fluorescent dopant in the EML2 364, respectively. Beside, each of the excited state singlet energy level $S_1^{TD}$ and the excited state triplet energy level $T_1^{TD}$ of the delayed fluorescent dopant in the EML2 364 is higher than each of the excited state singlet energy level $S_1 FD$ and the excited state triplet energy level $T_1^{FD}$ of the fluorescent dopant in the EML1 362, respectively.

If the EML 360 does not satisfy the above-mentioned energy level conditions, there exists a quenching phenomenon at both the delayed fluorescent dopant and the fluorescent dopant and/or the energy from the delayed fluorescent dopant cannot be transferred to the fluorescent dopant. As a result, the quantum efficiency of the OLED may be reduced.

In one exemplary embodiment, the energy bandgap between the excited state singlet energy level $S_1^{TD}$ and the excited state triplet energy level $T_1^{TD}$ may be equal to or less than about 0.3 eV. Besides, an energy level bandgap ($|HOMO^H - HOMO^{TD}|$) between a Highest Occupied Molecular Orbital energy level ($HOMO^H$) of the first and/or second hosts and a Highest Occupied Molecular Orbital energy level ($HOMO^{TD}$) of the delayed fluorescent dopant, or an energy level bandgap ($|LUMO^H - LUMO^{TD}|$) between a Lowest Unoccupied Molecular Orbital energy level ($LUMO^H$) of the first and/or second hosts and a Lowest Unoccupied Molecular Orbital energy level ($LUMO^{TD}$) of the first dopant may be equal to or less than about 0.5 eV.

In an alternatively exemplary embodiment, the first host, which is included in the EML1 362 together with the first fluorescent dopant, i.e. the organic compound represented by any of Chemical Formulae 1 to 2, may be the same material as the EBL 355. In this case, the EML1 362 may have an electron blocking function as well as an emission function. In other words, the EML1 362 can act as a buffer layer for blocking electrons. In one embodiment, in which the EML1 362 is an electron blocking layer as well as an emitting material layer, the EBL 355 may also be omitted.

In another exemplary embodiment, the EML1 362 may include the second host and the delayed fluorescent dopant, while the EML2 364 may include the first host and the first fluorescent dopant, that is the organic compound represented by any of Chemical Formulae 1 to 2. In this embodiment, the first host in the EML2 364 may be the same material as the HBL 375. In this case, the EML2 364 may have a hole blocking function as well as an emission function. In other words, the EML2 364 can act as a buffer layer for blocking holes. In one embodiment, the HBL 375 may be omitted where the EML2 364 may be a hole blocking layer as well as an emitting material layer.

Figure 12:
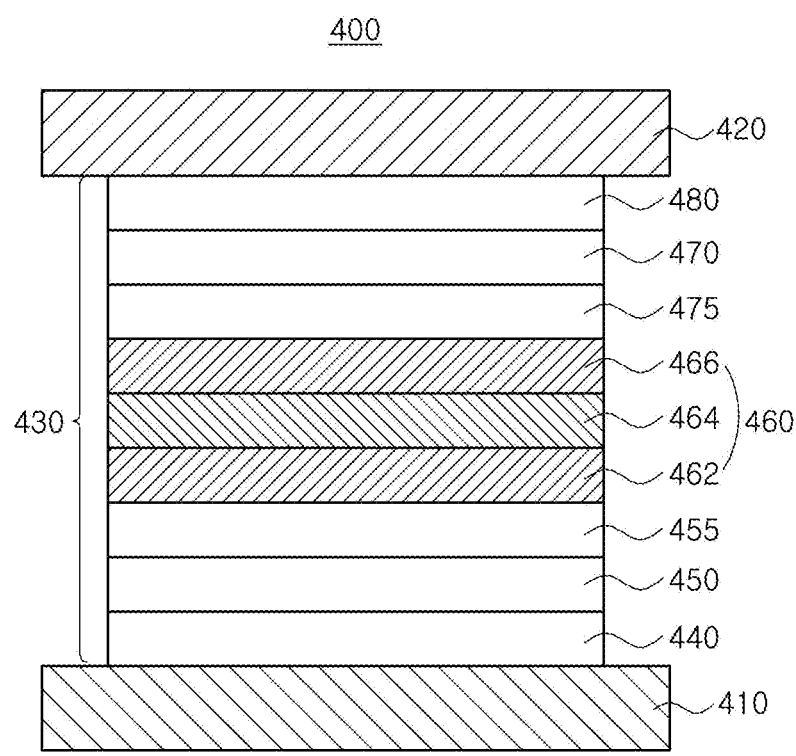
FIG. 12 is a schematic cross-sectional view illustrating an organic light-emitting diode in accordance with another exemplary embodiment of the present disclosure.

An OLED having a three-layered EML will be explained. FIG. 12 is a schematic cross-sectional view illustrating an organic light-emitting diode having a triple-layered EML in accordance with another exemplary embodiment of the present disclosure. As illustrated in FIG. 12, an OLED 400 in accordance with fifth embodiment of the present disclosure includes first and second electrodes 410 and 420 facing each other and an emission layer 430 disposed between the first and second electrodes 410 and 420.

In one exemplary embodiment, the emission layer 430 includes an HL 440, an HTL 450, and EML 460, an ETL 470 and an EL 480 each of which is laminated sequentially over the first electrode 410. Beside, the emission layer 430 may include an EBL 455 as a first exciton blocking layer disposed between the HTL 450 and the EML 460, and/or an HBL 475 as a second exciton blocking layer disposed between the EML 460 and the ETL 470.

In this embodiment, the EML 460 includes a first EML (EML1) 462 disposed between the EBL 455 and the HBL 475, a second EML (EML2) 464 disposed between the EML1 462 and the HBL 475 and a third EML (EML3) 466 disposed between the EML2 464 and the HBL 475. Each of the EML1 462 and the EML3 466 includes a first fluorescent dopant (F dopant 1) and a second fluorescent dopant 2 (F dopant 2), respectively, and the EML2 464 includes a delayed fluorescent dopant. For example, each of the first fluorescent dopant and the second fluorescent dopant may be the organic compound represented by any of Chemical Formulae 1 to 2, respectively. In this case, an excited state singlet energy level $S_1$ of the delayed fluorescent dopant in the EML2 464 may be higher than excited state energy levels $S_1^{FD1}$ and $S_1^{FD2}$ of the first and second fluorescent dopants each of which is included in the EML1 462 and EML3 466, respectively (See, FIG. 11). Each of the EML1 462, EML2 464 and EML3 466 further includes a first host, a second host and a third host, respectively.

In accordance with this embodiment, both the singlet energy and the triplet energy of the delayed fluorescent dopant in EML2 464 can be transferred to the first and second fluorescent dopants each of which is included in the EML1 462 and EML3 466 disposed adjacently to the EML2 464 by the FRET energy transfer mechanism. Accordingly, the ultimate emission occurs at the first and second fluorescent dopants in the EML1 462 and the EML3 466.

Figure 13:
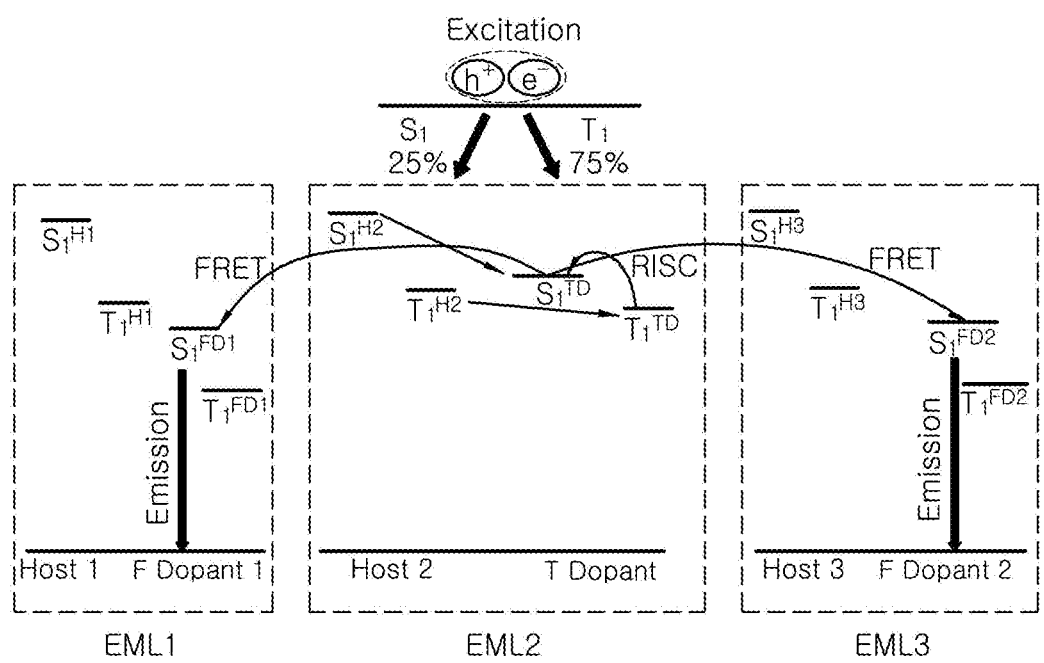
FIG. 13 is a schematic diagram illustrating luminous mechanism by energy level bandgap among a host, a delayed fluorescent dopant and a fluorescent material in an EML in accordance with another exemplary embodiment of the present disclosure.

In other words, the triplet energy of the delayed fluorescent dopant is converted to the singlet energy of the delayed fluorescent dopant in the EML2 464 by RISC, and the singlet energy of the delayed fluorescent dopant is transferred to the singlet energy of the first and second fluorescent dopants because the excited state singlet energy level $S_1^{TD}$ of the delayed fluorescent dopant is higher than the excited state singlet energy levels $S_1^{FD1}$ and $S_1^{FD2}$ of the first and second fluorescent dopants (See, FIG. 13). The first and second fluorescent dopants in the EML1 462 and EML3 466 can emit light both using the singlet energy and the triplet energy. Therefore, the OLED 400 has enhanced luminous efficiency and color purity due to the narrow FWHM of the first and second fluorescent dopants.

In this case, the delayed fluorescent dopant only acts as transferring energy to the first and second fluorescent dopants. The EML2 464 which includes the delayed fluorescent dopant is not involved in the ultimate emission process, while both the EML1 462 including the first fluorescent dopant and the EML3 466 including the second fluorescent dopant emit light.

Each of the EML1 462, the EML2 464 and the EML3 466 includes the first host, the second host and the third host, respectively. For example, each of the first host, the second host and the third host may respectively include, but is not limited to, mCP-CN, CBP, mCBP, MCP, DPEPO, PPT, TmPyPB, PYD-2CZ, DCzDBT, DCzTPA, pCzB-2CN, mCzB-2CN, TPSO1, CCP, 4-(3-(triphenylen-2-yl)phenyl) dibenzo[b,d]thiophene, 9-(4-(9H-carbazol-9-yl)phenyl)-9H-3,9'-bicarbazole, 9-(3-(9H-carbazol-9-yl)phenyl)-9H-3,9'-bicarbazole and/or 9-(6-(9H-carbazol-9-yl)pyridin-3-yl)-9H-3,9'-bicarbazole.

Beside, the delayed fluorescent dopant, which can be included in the EML2 464, may include, but is not limited to, Cz2BP, DcrTrZ, 4-DcrTrZ, 10-(4-(4,6-diphenyl-1,3,5-triazin-2-yl)phenyl)-10H-spiro[acridine-9,9'-xanthene], 2CzPN, 4CzIPN, 4CzPN, Px-VPN, TczTRZ and/or 32aIC-TRZ).

In one exemplary embodiment, each of the first to third hosts may have a higher weight ratio than the first fluorescent dopant, the delayed fluorescent dopant and the second fluorescent dopant in the EML1 462, the EML2 464 and the EML3 466, respectively. Besides, the weight ratio of the delayed fluorescent dopant in the EML2 464 may be higher than the weight ratio of the first fluorescent dopant in the EML1 462 and of the second fluorescent dopant in the EML3 466. In this case, it is possible to transfer enough energy from the delayed fluorescent dopant in the EML2 464 to the first fluorescent dopant in the EML1 462 and to the second fluorescent dopant in the EML3 466.

Energy level relationships among the materials in the EML 460 including three EMLs 462, 464, and 466 will be explained. FIG. 13 is a schematic diagram illustrating a luminous mechanism by energy level bandgap among a host, a delayed fluorescent dopant and a fluorescent material in a triple-layered EML in accordance with another exemplary embodiment of the present disclosure. As illustrated in FIG. 13, each of an excited state singlet energy level $S_1^{H1}$ and an excited state triplet energy level $T_1^{H1}$ of the first host is higher than each of an excited state singlet energy level $S_1^{FD1}$ and an excited state triplet energy level $T_1^{FD}$ of the first fluorescent dopant in the EML1 462, respectively. Besides, each of an excited state singlet energy level $S_1^{H3}$ and an excited state triple energy level $T_1^{H3}$ of the third host is higher than each of an excited state singlet energy level $S_1^{FD2}$ and an excited state triplet energy level $T_1^{FD2}$ of the second fluorescent dopant in the EML3 466.

Also, each of an excited state singlet energy level $S_1^{H2}$ and an excited state triplet energy level $T_1^{H2}$ of the second host are higher than each of an excited state singlet energy level $S_1^{TD}$ and an excited state triplet energy level $T_1^{TD}$ of the delayed fluorescent dopant in the EML2 464, respectively. Besides, each of an excited state triplet energy level $T_1^{H1}$ of the first host in the EML1 462 and an excited state triplet energy level $T_1^{H3}$ of the third host in the EML3 466 is higher than the excited state triplet energy level $T_1^{TD}$ of the delayed fluorescent dopant in the EML2 464. Also, each of an excited state singlet energy level $S_1^{H1}$ of the first host in the EML1 462 and an excited state singlet energy level $S_1^{H3}$ of the third host in the EML3 466 may be higher than the excited state singlet energy level $S_1^{TD}$ of the delayed fluorescent dopant in the EML2 464. In addition, the excited state singlet energy level $S_1^{TD}$ of the delayed fluorescent dopant in the EML2 464 is higher than the excited state singlet energy levels $S_1^{FD1}$ and $S_1^{FD2}$ of the first and second fluorescent dopants in the EML1 462 and the EML3 466.

In one exemplary embodiment, the energy bandgap between the excited state singlet energy level $S_1^{TD}$ and the excited state triplet energy level $T_1^{TD}$ may be equal to or less than about 0.3 eV. Besides, an energy level bandgap (|HOMO$^H$−HOMO$^{TD}$|) between a Highest Occupied Molecular Orbital energy level (HOMO$^H$) of the first, second and/or third hosts and a Highest Occupied Molecular Orbital energy level (HOMO$^{TD}$) of the delayed fluorescent dopant, or an energy level bandgap (|LUMO$^H$−LUMO$^{TD}$|) between a Lowest Unoccupied Molecular Orbital energy level (LUMO$^H$) of the first, second and/or third hosts and a Lowest Unoccupied Molecular Orbital energy level (LUMO$^{TD}$) of the first dopant may be equal to or less than about 0.5 eV.

In an alternatively exemplary embodiment, the first host, which is included in the EML1 462 together with the first fluorescent dopant, i.e. the organic compound represented by any of Chemical Formulae 1 to 2, may be the same material as the EBL 455. In this case, the EML1 462 may have an electron blocking function as well as an emission function. In other words, the EML1 462 can act as a buffer layer for blocking electrons. In one embodiment, in which the EML1 462 is an electron blocking layer as well as an emitting material layer, the EBL 455 may also be omitted.

In another exemplary embodiment, the third host, which is included in the EML3 466 together with the second fluorescent dopant, i.e., the organic compound represented by any of Chemical Formulae 1 to 2, may be the same material as the HBL 475. In this case, the EML3 466 may have a hole blocking function as well as an emission function. In other words, the EML3 466 can act as a buffer layer for blocking holes. In one embodiment, in which the EML3 466 is a hole blocking layer as well as an emitting material layer, the HBL 475 may also be omitted.

In still another exemplary embodiment, the first host in the EML1 462 may be the same material as the EBL 455 and the third host in the EML3 466 may be the same material as the HBL 475. In this embodiment, the EML1 462 may have an electron blocking function as well as an emission function, and the EML3 466 may have a hole blocking function as well as an emission function. In other words, each of the EML1 462 and the EML3 466 can act as a buffer layer for blocking electrons or hole, respectively. In one embodiment, in which the EML1 462 is an electron blocking layer as well as an emitting material layer and the EML3 466 is a hole blocking layer as well as an emitting material layer, the HBL 475 and the EBL 455 may also be omitted.

Synthesis Example 1: Synthesis of Compound 1

(1) Synthesis of Intermediate A

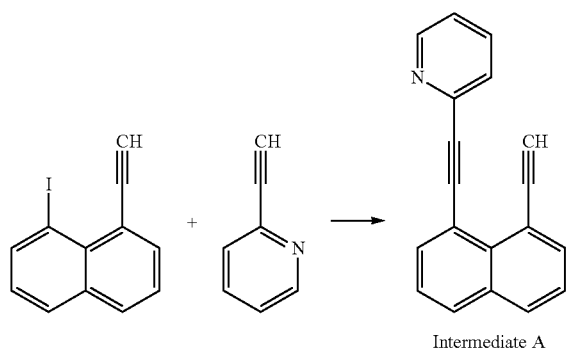

Intermediate A

1-Ethinyl-8-iodo-naphthalene (CAS Registry No. 18083-66-4) was mixed with 2-Ethinylpyridine (CAS Registry No. 1945-82-4) in a 1:1.5 molar ratio in a 2 L round bottom flask under $N_2$ purging condition, and the mixture was dissolved in Triethylamine (CAS Registry No. 121-44-8). Then, Bis-triphenylphosphine-palladium (II) chloride, Copper (I) iodide and Triphenylphosphine were added to the mixture solution so as to proceed the reaction and the reaction mixture was refluxed and stirred for 11 hours at 40° C. so as to proceed Sonogashira Coupling reaction. After the reaction is completed, the solution was cooled to room temperature, the precipitate was filtered and the solvent was dried to obtain a solid. The solid was extracted with Dichloromethane/DI water, and water was removed with $MgSO_4$. After removing the organic solvent, the solid was purified using dichloromethane/hexane as a developing solvent and recrystallized to give intermediate A.

(2) Synthesis of Compound 1

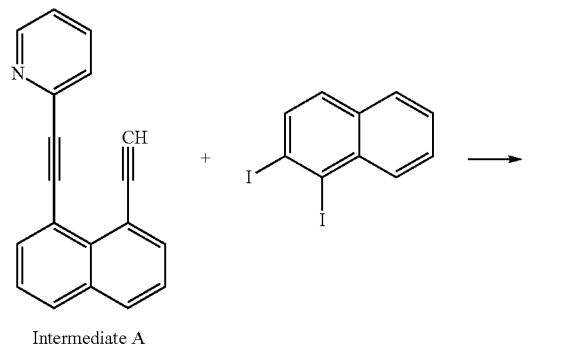

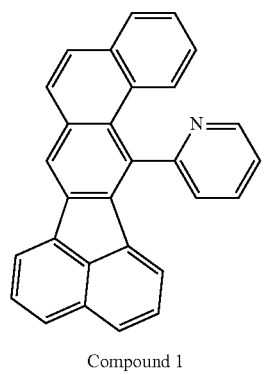

Compound 1

Intermediate A was mixed with 1,2-Diiodonaphthalene (CAS Registry No. 27715-42-0) in a 1:1.5 molar ratio under $N_2$ purging condition, and then the mixture was dissolved in toluene. Then, a 0.05 molar ratio of $Pd(OAc)_2$ (Palladium (II) acetate) based on the intermediate A and a 2 molar ratio of AgOAc (silver acetate) based on the intermediate A were added to the mixture so as to proceed the reaction and the reaction mixture was refluxed and stirred for 16 hours at 110-130° C. After the reaction was completed, the solution was cooled to room temperature, the precipitate was filtered and washed with methanol. The obtained yellow solid was recrystallized with toluene/hexane to give Compound 1 (yield 20%).

Synthesis Example 2: Synthesis of Compound 6

(1) Synthesis of Intermediate B

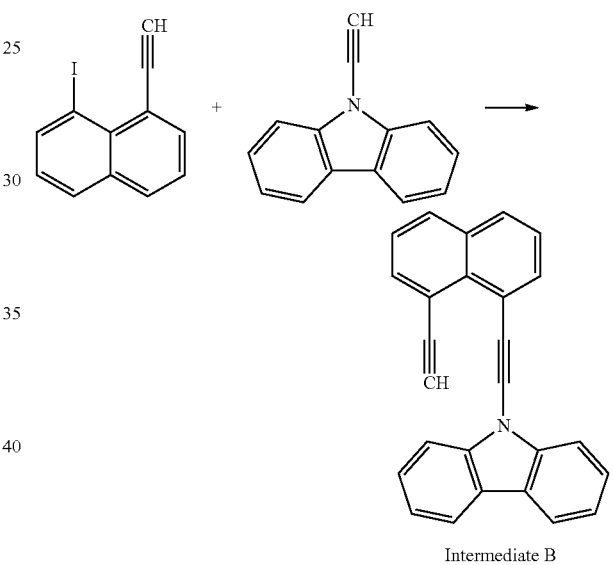

Intermediate B

1-Ethinyl-8-iodo-naphthalene (CAS Registry No. 18083-66-4) was mixed with 9-ethynyl-9H-carbazole (CAS Registry No. 26157-62-0) in a 1:1.5 molar ratio in a 2 L round bottom flask under $N_2$ purging condition, and the mixture was dissolved in Triethylamine. Then, Bis-triphenylphosphine-palladium (II) chloride, Copper (I) iodide and Triphenylphosphine were added to the mixture solution so as to proceed the reaction and the reaction mixture was refluxed and stirred for 11 hours at 40° C. so as to proceed Sonogashira Coupling reaction. After the reaction is completed, the solution was cooled to room temperature, the precipitate was filtered and the solvent was dried to obtain solid. The solid was extracted with Dichloromethane/DI water, and water was removed with $MgSO_4$. After removing the organic solvent, the solid was purified using dichloromethane/hexane as a developing solvent and recrystallized to give intermediate B.

(2) Synthesis of Compound 6

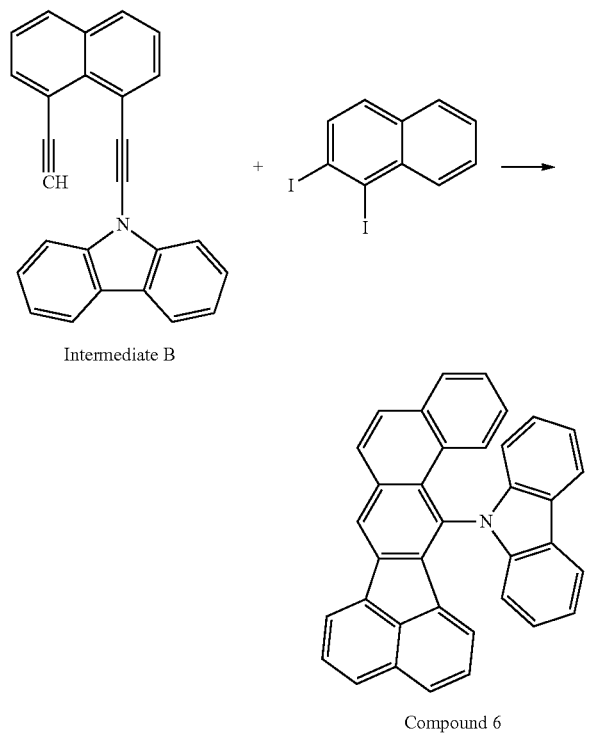

Intermediate B

Compound 6

Intermediate B was mixed with 1,2-Diiodonaphthalene (CAS Registry No. 27715-42-0) in a 1:1.5 molar ratio under N₂ purging condition, and then the mixture was dissolved in toluene. Then, a 0.05 molar ratio of Pd(OAc)₂ based on the intermediate B and a 2 molar ratio of AgOAc based on the intermediate B were added to the mixture so as to proceed the reaction and the reaction mixture was refluxed and stirred for 16 hours at 110-130° C. After the reaction was completed, the solution was cooled to room temperature, the precipitate was filtered and washed with methanol. The obtained yellow solid was recrystallized with toluene/hexane to give Compound 6 (yield 20%).

Synthesis Example 3: Synthesis of Compound 12

(1) Synthesis of Intermediate C

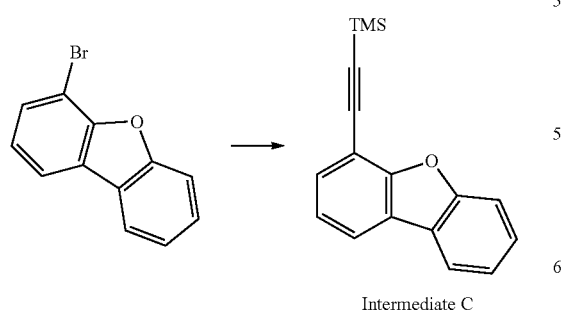

Intermediate C

4-Bromodibenzofuran (CAS Registry No. 89827-45-2) was mixed with Ethynyltrimethylsilane (CAS Registry No. 1066-54-2) in a 1:1.5 molar ratio in a 2 L round bottom flask under N₂ purging condition, and the mixture was dissolved in Triethylamine. Then, [1,1'-Bis(diphenylphosphine)ferrocene]dichloropalladium (IIto) chloride (CAS Registry No. 72287-26-4), Copper (I) iodide (CAS Registry No. 7681-65-4), Triphenylphosphine (CAS Registry No. 603-35-9) and Triethylamine were added to the mixture solution so as to proceed the reaction and the reaction mixture was refluxed and stirred for 5 hours at 40° C. After the reaction is completed, the solution was cooled to room temperature, and heptane (CAS Registry No. 142-82-5) was added to terminate the reaction. The resulting product was filtered with spreading celite and silica gel pad, and the solvent was dried to give intermediate C.

(2) Synthesis of Intermediate D

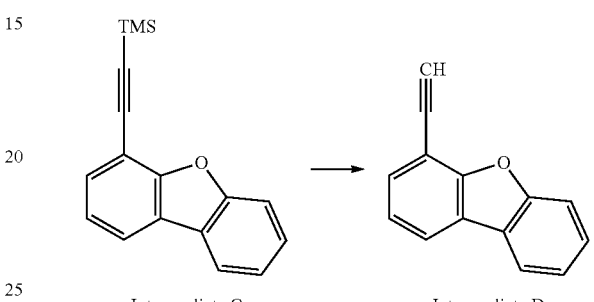

Intermediate C    Intermediate D

Intermediate C was mixed with Potassium carbonate (CAS Registry No. 584-08-7) in a 1:1.5 molar ration in a 2 L round bottom flask under N₂ purging condition, and the mixture was dissolved in a mixed solution of methanol/Tetrahydrofuran (1:1). The solution was refluxed and stirred for 2 hours at room temperature. After the reaction was completed, heptane was added to terminate the reaction. The resulting product was filtered and the solvent was dried to obtain solid. The solid was extracted with ethylacetate/DI water, water was removed with MgSO₄ and filtered to give oil type intermediate D.

(3) Synthesis of Intermediate E

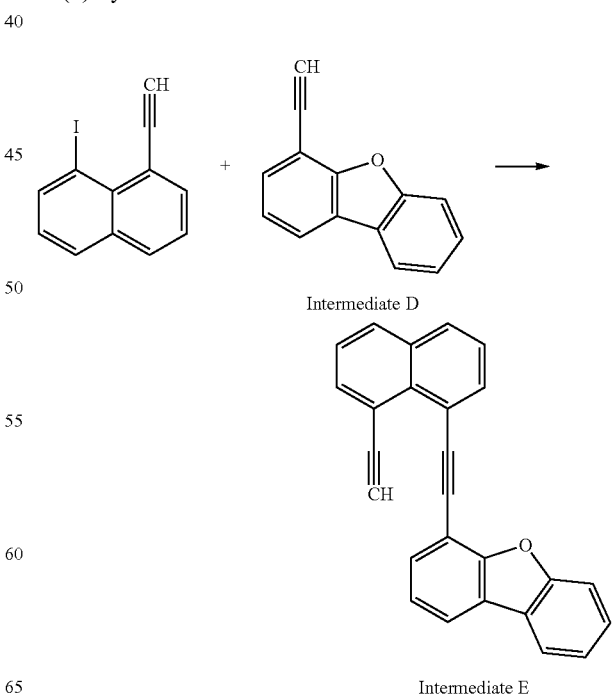

Intermediate D

Intermediate E

1-Ethinyl-8-iodo-naphthalene (CAS Registry No. 18083-66-4) was mixed with Intermediate D in a 1:1.5 molar ratio in a 2 L round bottom flask under $N_2$ purging condition, and the mixture was dissolved in Triethylamine. Then, Bis-triphenylphosphine-palladium (II) chloride, Copper (I) iodide and Triphenylphosphine were added to the mixture solution so as to proceed the reaction and the reaction mixture was refluxed and stirred for 11 hours at 40° C. so as to proceed Sonogashira Coupling reaction. After the reaction is completed, the solution was cooled to room temperature, the precipitate was filtered and the solvent was dried to obtain solid. The solid was extracted with Dichloromethane/DI water, and water was removed with $MgSO_4$. After removing the organic solvent, the solid was purified using dichloromethane/hexane as a developing solvent and recrystallized to give intermediate E.

(4) Synthesis of Compound 12

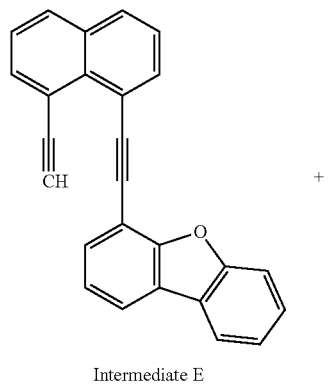

Intermediate E

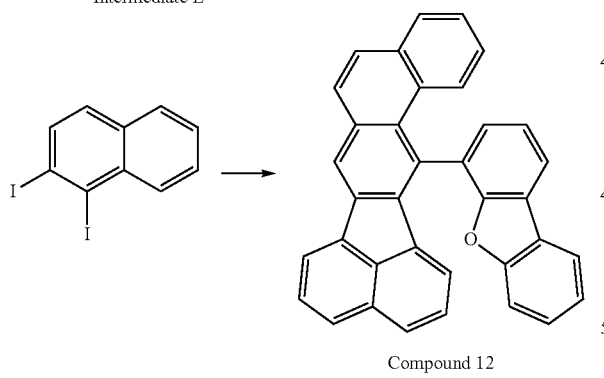

Compound 12

Intermediate E was mixed with 1,2-Diiodonaphthalene (CAS Registry No. 27715-42-0) in a 1:1.5 molar ratio under $N_2$ purging conditions, and then the mixture was dissolved in toluene. Then, a 0.05 molar ratio of $Pd(OAc)_2$ based on the intermediate E and a 2 molar ratio of AgOAc based on the intermediate E were added to the mixture so as to proceed the reaction and the reaction mixture was refluxed and stirred for 16 hours at 110-130° C. After the reaction was completed, the solution was cooled to room temperature, and the precipitate was filtered and washed with methanol. The obtained yellow solid was recrystallized with toluene/hexane to give Compound 12 (yield 40%).

Synthesis Example 4: Synthesis of Compound 15

(1) Synthesis of Intermediate F

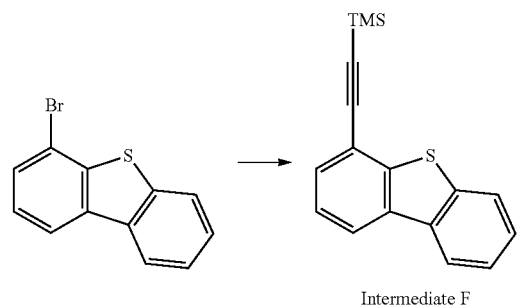 [SMILES: Brc1cccc2c1sc1ccccc12 ; C[Si](C)(C)C#Cc1cccc2c1sc1ccccc12]

Intermediate F

4-Bromodibenzothiophene (CAS Registry No. 97511-05-2) was mixed with Ethynyltrimethylsilane (CAS Registry No. 1066-54-2) in a 1:1.5 molar ratio in a 2 L round bottom flask under $N_2$ purging condition, and the mixture was dissolved in Triethylamine. Then, [1,1'-Bis(diphenylphosphine)ferrocene]dichloropalladium (II) chloride (CAS Registry No. 72287-26-4), Copper (I) iodide (CAS Registry No. 7681-65-4), Triphenylphosphine (CAS Registry No. 603-35-9) and Triethylamine were added to the mixture solution so as to proceed the reaction and the reaction mixture was refluxed and stirred for 5 hours at 40° C. After the reaction is completed, the solution was cooled to room temperature, and heptane (CAS Registry No. 142-82-5) was added to terminate the reaction. The resulting product was filtered with spreading celite and silica gel pad, and the solvent was dried to give intermediate F.

(2) Synthesis of Intermediate G

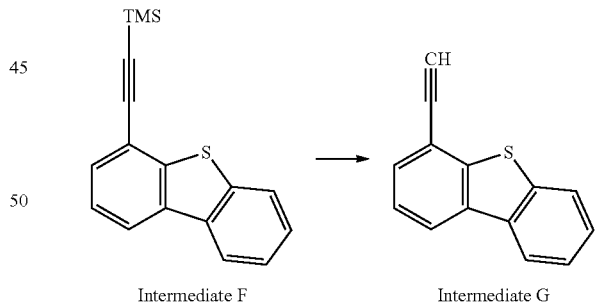

Intermediate F        Intermediate G

Intermediate F was mixed with Potassium carbonate (CAS Registry No. 584-08-7) in a 1:1.5 molar ration in a 2 L round bottom flask under $N_2$ purging conditions, and the mixture was dissolved in a mixed solution of methanol/Tetrahydrofuran (1:1). The solution was refluxed and stirred for 2 hours at room temperature. After the reaction was completed, heptane was added to terminate the reaction. The resulting product was filtered and the solvent was dried to obtain solid. The solid was extracted with ethylacetate/DI water and water was removed with $MgSO_4$ and filtered to give oil type intermediate G.

(3) Synthesis of Intermediate H

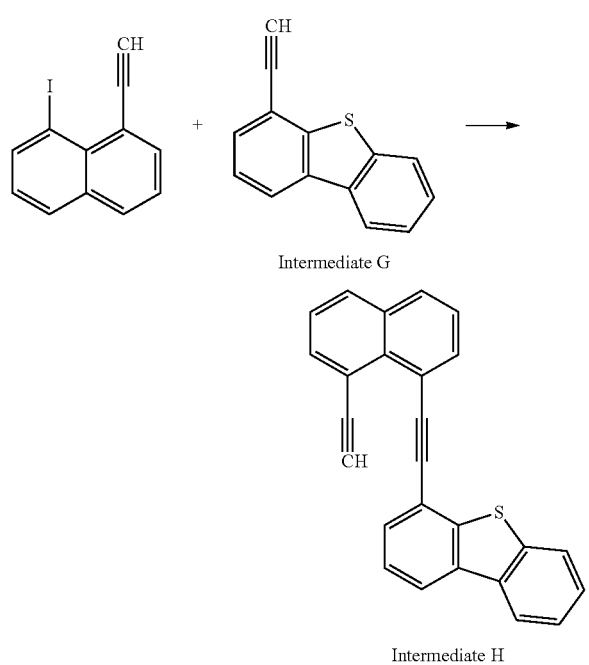

Intermediate G

Intermediate H

1-Ethynyl-8-iodo-naphthalene (CAS Registry No. 18083-66-4) was mixed with Intermediate G in a 1:1.5 molar ratio in a 2 L round bottom flask under $N_2$ purging condition, and the mixture was dissolved in Triethylamine. Then, Bis-triphenylphosphine-palladium (II) chloride, Copper (I) iodide and Triphenylphosphine were added to the mixture solution so as to proceed the reaction and the reaction mixture was refluxed and stirred for 11 hours at 40° C. so as to proceed Sonogashira Coupling reaction. After the reaction is completed, the solution was cooled to room temperature, the precipitate was filtered and the solvent was dried to obtain solid. The solid was extracted with Dichloromethane/DI water, and water was removed with $MgSO_4$. After removing the organic solvent, the solid was purified using dichloromethane/hexane as a developing solvent and recrystallized to give intermediate H.

(4) Synthesis of Compound 15

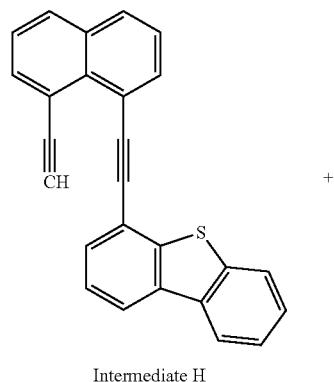

Intermediate H

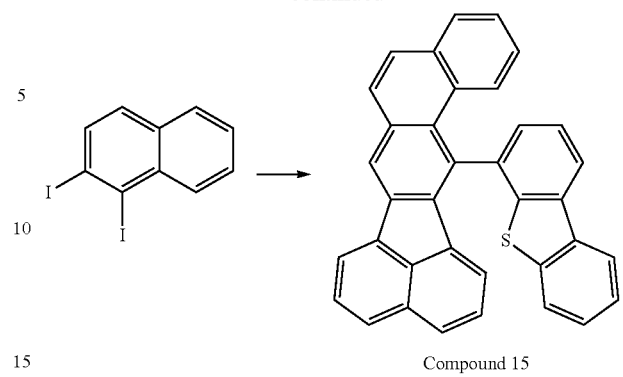

Compound 15

Intermediate H was mixed with 1,2-Diiodonaphthalene (CAS Registry No. 27715-42-0) in a 1:1.5 molar ratio under $N_2$ purging conditions, and then the mixture was dissolved in toluene. Then, a 0.05 molar ratio of $Pd(OAc)_2$ based on the intermediate E and a 2 molar ratio of AgOAc based on the intermediate E were added to the mixture so as to proceed the reaction and the reaction mixture was refluxed and stirred for 16 hours at 110-130° C. After the reaction was completed, the solution was cooled to room temperature, the precipitate was filtered and washed with methanol. The obtained yellow solid was recrystallized with toluene/hexane to give Compound 15 (yield 32%).

Experimental Example: Measurement of Stokes Shift of Organic Compound

UV Wavelength of Maximum absorption (UV $\lambda_{max}$), wavelength of Maximum Photoluminescence (PL $\lambda_{max}$) and Stokes Shift for Compound 1, Compound 6 and Compound 12, each of which were synthesized respectively in Synthesis Examples 1 to, 3 were measured so as to evaluate luminous properties of those compounds. Also, UV $\lambda_{max}$, PL $\lambda_{max}$ and Stokes Shift for the following compounds (References 1 to 5) were measured for comparison. Each of the compounds was dissolved in toluene solution for evaluating the luminous properties.

Reference 1

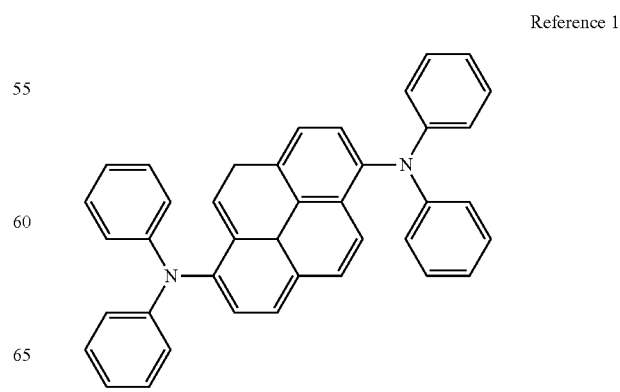

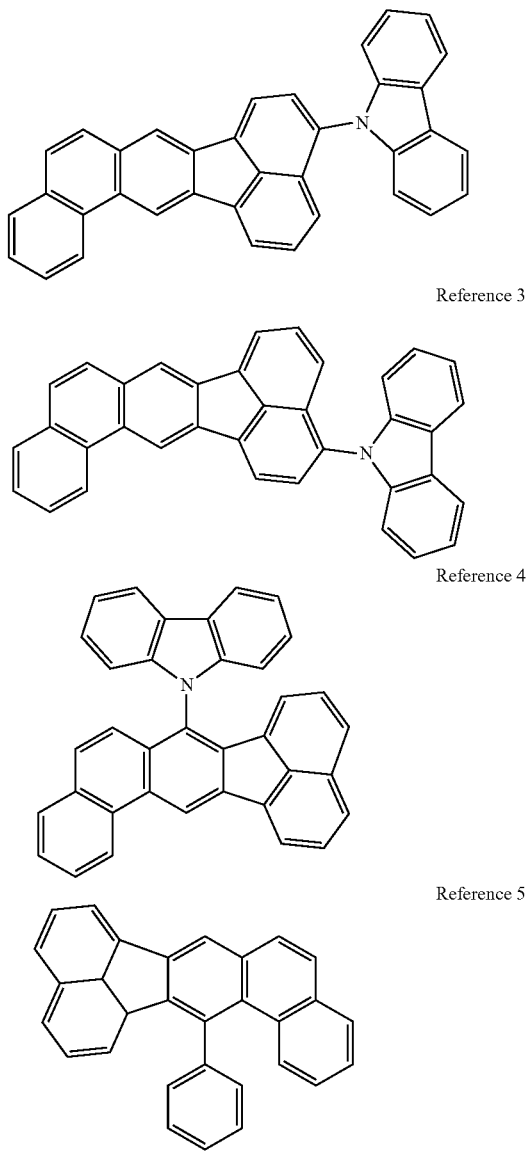

The measurement results are indicated in the following Table 1. As indicated by Table 1, Reference 1 compound, which is a prior art fluorescent dopant having a pyrene core, showed UV $\lambda_{max}$ that was located at significantly short wavelength compared to its PL $\lambda_{max}$ and, therefore, showed a very large Stokes Shift. While each of Reference compounds 2 to 4 having naphtho-fluoranthene core showed adjusted PL $\lambda_{max}$, its UV $\lambda_{max}$ was very shorter compared to its PL $\lambda_{max}$, and, therefore Reference compounds 2 to 4 still showed relatively large Stokes Shift. It seems as if the positions of the hetero aromatic group for adjusting color sensitivity (corresponding to $R_1$ to $R_3$ positions bonded to the naphtho-fluoranthene core in Chemical Formula 1) had an effect on such results. In addition, while Reference compound 5 having a naphtho-fluoranthene core showed reduced Stokes Shift, its PL $\lambda_{max}$ and UV $\lambda_{max}$ was located at relatively short wavelengths, and therefore, was not proper for implementing blue emission having high color purity. It seems that the position of the aromatic group (corresponding to the X position bonded to the naphtho-fluoranthene core in Chemical Formula 1) may have an effect on such a result. In contrast, all the Compound 1, Compound 6 and Compound 12 showed small Stokes Shift and had proper UV $\lambda_{max}$ and PL $\lambda_{max}$) for implementing blue emission having high color purity.

TABLE 1

Emission Properties of Organic Compound

| Sample | UV $\lambda_{max}$ (nm) | PL $\lambda_{max}$ (nm) | Stokes Shift (nm) |
|---|---|---|---|
| Reference 1 | 424 | 461 | 37 |
| Reference 2 | 430 | 458 | 28 |
| Reference 3 | 431 | 458 | 27 |
| Reference 4 | 432 | 455 | 22 |
| Reference 5 | 425 | 434 | 9 |
| Compound 1 | 440 | 452 | 12 |
| Compound 6 | 437 | 448 | 11 |
| Compound 12 | 439 | 453 | 14 |

Example 1: Manufacture of Organic Light-Emitting Diode (OLED)

An organic light-emitting diode was manufacture using Compound 1 synthesized in the Synthesis Example 1 as a dopant in an emitting material layer (EML). A glass substrate was washed by UV-Ozone treatment before using, and was transferred to a vacuum chamber for depositing emission layer. Subsequently, an anode, an emission layer and a cathode were deposited in the following order of mention: An anode (ITO, 500 Å); a hole injection layer (HIL) (HAT-CN; 50 Å); a hole transport layer (HTL) (NPB, 500 Å); an electron blocking layer (EBL) (2,8-bis(9-phenyl-9H-carbazol-3-yl)dibenzo[b,d]thiophene; 100 Å); an emitting material layer (EML) (DPEPO (host): Cz2BP (delayed fluorescent dopant): Compound 1 (fluorescent dopant)=69:30:1 by weight ratio); 300 Å); a hole blocking layer (HBL) (DPEPO; 100 Å); an electron transport layer (ETL) (TPBi; 250 Å); an electron injection layer (EIL) (LiF; 50 Å); and a cathode (Al; 1000 Å).

And then, a capping layer (CPL) was deposited over the cathode and the device was encapsulated by glass. After deposition of the emissive layer and the cathode, the OLED was transferred from the deposition chamber to a dry box for film formation, followed by encapsulation using UV-curable epoxy and moisture getter. The manufacture organic light-emitting diode had an emission area of 9 mm².

Examples 2 to 3: Manufacture of OLED

An organic light-emitting diode was manufactured according to the same process and with the same materials as in Example 1, except that Compound 6 (Example 2) synthesized in Synthesis Example 2 and Compound 12 (Example 3) synthesized in Synthesis Example 3 were used as the fluorescent dopant in the EML instead of Compound 1.

Comparative Examples 1 to 5: Manufacture of OLED

An organic light-emitting diode was manufactured as the same process and the same materials as in Example 1, except that Reference Compounds 1 to 5 (Comparative Example 1 to 5) as the fluorescent dopant in the EML instead of the Compound 1.

Experimental Example 2: Measurement of Luminous Properties of OLED

Each of the organic light-emitting diode with manufactured by Examples 1 to 3 and Comparative Examples 1 to 5 was connected to an external power source, and luminous properties for all the diodes were evaluated using a constant current source (KEITHLEY) and a photometer PR650 at room temperature. In particular, driving voltage (V), current efficiency (cd/A), power efficiency (lm/W), external quantum efficiency (EQE; %), color coordinates and maximum electroluminescent wavelength (EL $\lambda_{max}$; nm) at a current density of 10 mA/cm² of the light-emitting diodes of Examples 1 to 3 and Comparative Examples 1 to 5 were measured. The results thereof are shown in the following Table 2.

TABLE 2

Luminous Properties of OLED

| Sample | V | cd/A | lm/W | EQE (%) | CIEx | CIEy | EL $\lambda$max |
|---|---|---|---|---|---|---|---|
| Comparative Example 1 | 4.5 | 9.2 | 6.4 | 4.9 | 0.143 | 0.245 | 465 |
| Comparative Example 2 | 4.9 | 17.3 | 11.1 | 6.1 | 0.163 | 0.210 | 460 |
| Comparative Example 3 | 5.0 | 17.2 | 10.8 | 5.9 | 0.170 | 0.210 | 461 |
| Comparative Example 4 | 4.8 | 17.1 | 11.2 | 6.5 | 0.161 | 0.208 | 459 |
| Comparative Example 5 | 4.6 | 10.5 | 7.2 | 5.7 | 0.144 | 0.150 | 435 |
| Example 1 | 5.0 | 21.0 | 13.2 | 14.5 | 0.165 | 0.190 | 457 |
| Example 2 | 4.7 | 20.3 | 13.6 | 15.3 | 0.165 | 0.181 | 451 |
| Example 3 | 4.6 | 21.1 | 14.4 | 15.7 | 0.166 | 0.186 | 455 |

As indicated in Table 2, when Reference Compounds 1-5 having UV $\lambda_{max}$ shorter than 435 nm were used as the fluorescent dopant in EML, the OLED showed lower luminous efficiency because of lower energy transfer efficiencies from the emission state of the delayed fluorescent material to the absorption state of the Reference Compounds 1-5. Particularly, compared to the OLED using Reference Compound 1 having pyrene core as the fluorescent dopant in Comparative Example 1, the OLED using the organic compounds in Examples 1 to 3 as the fluorescent dopant enhanced current efficiency maximally by 129.3%, power efficiency maximally by 125.0% and EQE maximally by 220.4%. Compared to the OLED using Reference Compounds 2-4 in which the hetero aromatic group is substituted to positions not sterically adjacent to a conformationally bent naphtho moiety as the fluorescent dopant in Comparative Examples 2-4, the OLED using the organic compound in Examples 1 to 3 enhance current efficiency maximally by 23.4%, power efficiency maximally by 33.3% and EQE maximally by 166.1%. Besides, compared to the OLED using Reference Compound 5 in which the homo aromatic group is bonded to the naphtho fluoranthene core as the fluorescent dopant in Comparative Example 5, the OLED using the organic compound in Examples 1 to 3 enhance current efficiency maximally by 101.0%, power efficiency maximally by 100.0% and EQE maximally by 175.4%. Particularly, compared to the OLED using Reference Compound 5 as the fluorescent dopant, the OLED using the organic compounds as the fluorescent dopant can implement blue emission with high color purity.

From these results, it was confirmed that an organic light-emitting diode and an organic light-emitting device such as an organic light-emitting display device and an organic light-emitting illumination device using the organic compounds can enhance luminous efficiency and implement hyper-fluorescence with high color purity.

While the present disclosure has been described with reference to exemplary embodiments and examples, these embodiments and examples are not intended to limit the scope of the present disclosure. Rather, it will be apparent to those skilled in the art that various modifications and variations can be made in the present disclosure without departing from the spirit or scope of the invention. Thus, it is intended that the present disclosure cover the modifications and variations of the present disclosure provided they come within the scope of the appended claims and their equivalents.

The various embodiments described above can be combined to provide further embodiments. All of the U.S. patents, U.S. patent application publications, U.S. patent applications, foreign patents, foreign patent applications and non-patent publications referred to in this specification and/or listed in the Application Data Sheet are incorporated herein by reference, in their entirety. Aspects of the embodiments can be modified, if necessary to employ concepts of the various patents, applications and publications to provide yet further embodiments.

It will be apparent to those skilled in the art that various modifications and variations can be made in the organic compound, the organic light-emitting diode, and the organic light-emitting device having the compound of the present disclosure without departing from the technical idea or scope of the disclosure. Thus, it is intended that the present disclosure cover the modifications and variations of this disclosure provided they come within the scope of the appended claims and their equivalents.

The invention claimed is:

1. An organic light-emitting diode, comprising:
   a first electrode;
   a second electrode facing the first electrode; and
   a first emitting material layer between the first and second electrode,
   wherein the first emitting material layer includes an organic compound represented by the following Chemical Formula 1:

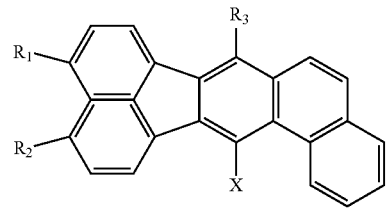

Chemical Formula 1 wherein each of $R_1$ to $R_3$ is independently selected from the group consisting of hydrogen, unsubstituted or substituted $C_1$-$C_{10}$ alkyl group, substituted or substituted $C_4$-$C_{30}$ alicyclic group and unsubstituted or substituted $C_5$-$C_{30}$ aromatic group, and wherein X is unsubstituted or substituted $C_4$-$C_{30}$ hetero aromatic group;
wherein the first emitting material layer further includes a first host and a first dopant, wherein the organic compound is used as a second dopant, and
wherein an excited state singlet energy level of the first dopant is higher than an excited state singlet energy level of the second dopant.

2. The organic light-emitting diode of claim 1, wherein an energy bandgap between an excited state single energy level of the first dopant and an excited state triplet energy level of the first dopant is equal to or less than about 0.3 eV.

3. The organic light-emitting diode of claim 1, an energy bandgap between a Highest Occupied Molecular Orbital energy level of the first host and a Highest Occupied Molecular Orbital energy level of the first dopant or an energy bandgap between a Lowest Unoccupied Molecular Orbital energy level of the first host and a Lowest Unoccupied Molecular Orbital energy level of the first dopant is equal to or less than about 0.5 eV.

4. The Organic light-emitting diode of claim 1, wherein an excited state triplet energy level of the first dopant is lower than an excited state triplet energy level of the first host and higher than an excited state triplet energy level of the second dopant.

5. An organic light-emitting device, comprising:
a substrate; and
an organic light-emitting diode according to claim 1 over the substrate.

6. The organic light-emitting device of claim 5, wherein the organic light-emitting device comprises an organic light-emitting display device and an organic light-emitting illumination device.

7. The organic light-emitting diode of claim 1, wherein X in Chemical Formula 1 is $C_4$-$C_{30}$ hetero aromatic group unsubstituted or substituted with at least one of $C_1$-$C_{10}$ alkyl group and $C_4$-$C_{30}$ aromatic or hetero aromatic group.

8. The organic light-emitting diode of claim 1, wherein the $C_4$-$C_{30}$ hetero aromatic group in Chemical Formula 1 is selected from the group consisting of $C_4$-$C_{30}$ hetero aryl group, $C_4$-$C_{30}$ hetero aralkyl group, $C_4$-$C_{30}$ hetero aryloxyl group and $C_4$-$C_{30}$ hetero aryl amino group, and each of the hetero aryl group, the hetero aralkyl group, the hetero aryloxyl group and the hetero aryl amino group is independently unsubstituted or substituted with at least one of $C_1$-$C_{10}$ alkyl group and $C_4$-$C_{30}$ aromatic or hetero aromatic group.

9. The organic light-emitting diode of claim 1, wherein each of $R_1$ to $R_3$ in Chemical Formula 1 is independently selected from the group consisting of hydrogen, methyl group, tert-butyl group, phenyl group and naphthyl group.

10. The organic light-emitting diode of claim 1, wherein X in Chemical Formula 1 has any one of the following structures:

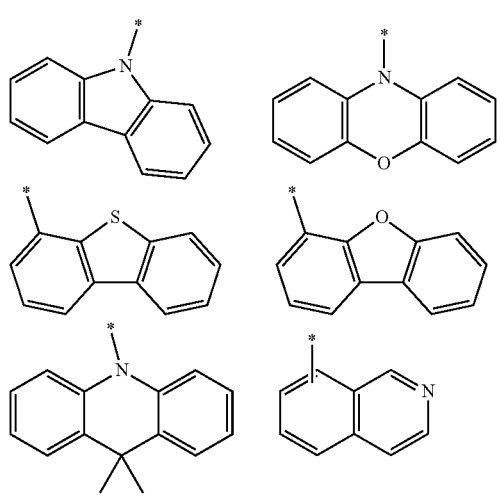

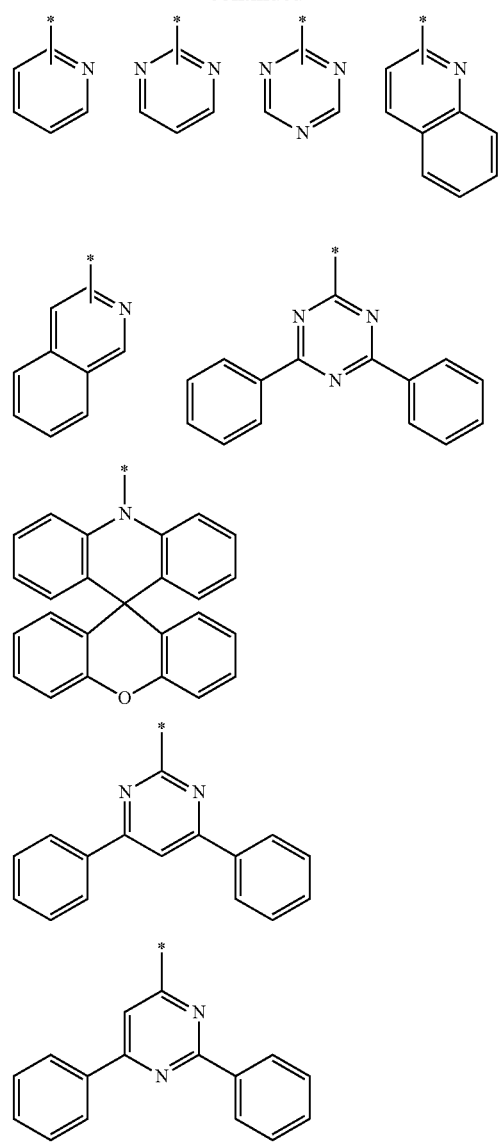

wherein the asterisk indicates a bonded portion.

11. The organic light-emitting diode of claim 1, wherein the organic compound has one of the following structures of Chemical Formula 2:

Chemical Formula 2

Compound 1

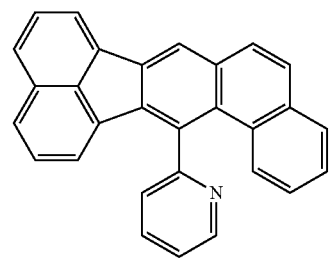

Compound 2
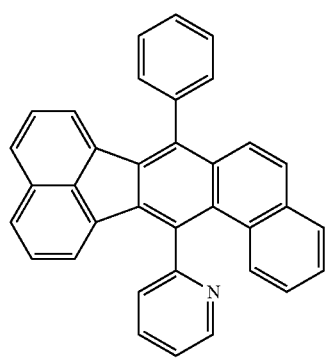
Compound 3
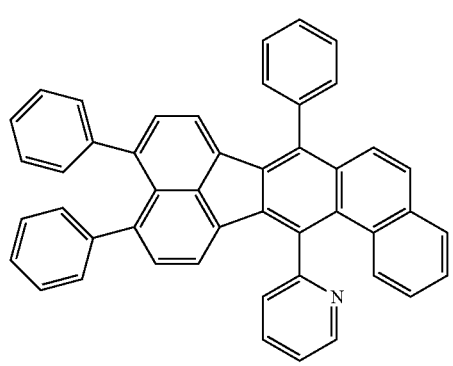
Compound 4
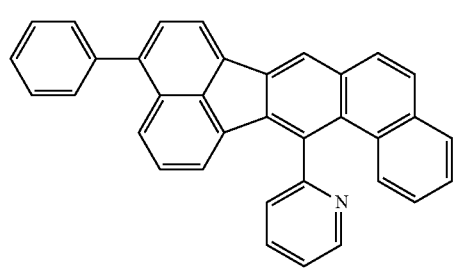
Compound 5
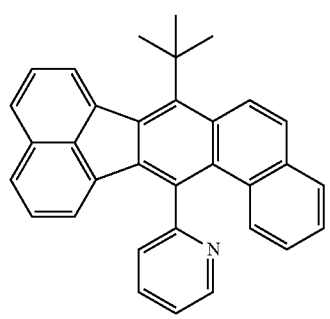
Compound 6
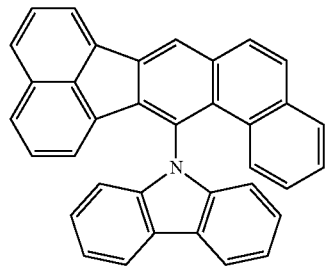
Compound 7
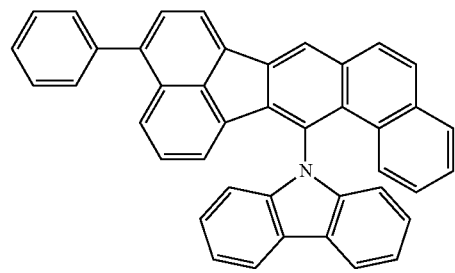
Compound 8
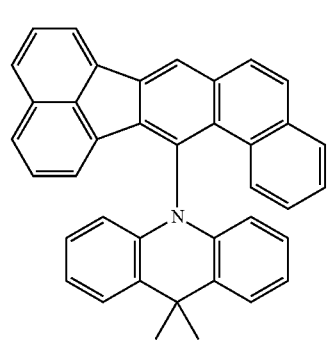
Compound 9
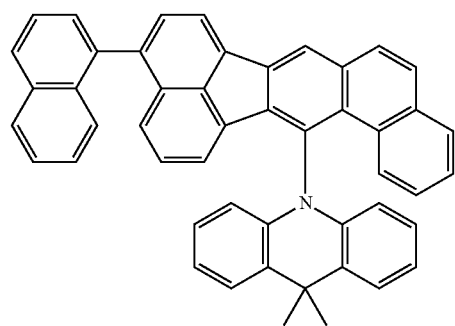
Compound 10
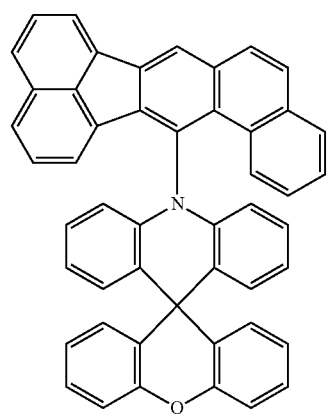

Compound 11
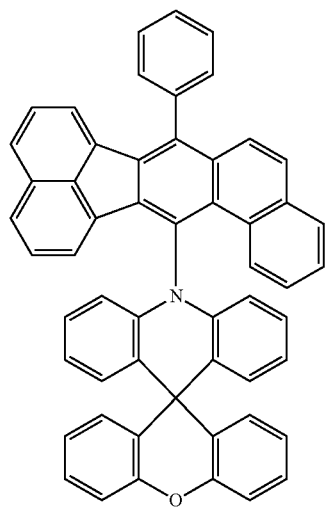
Compound 12
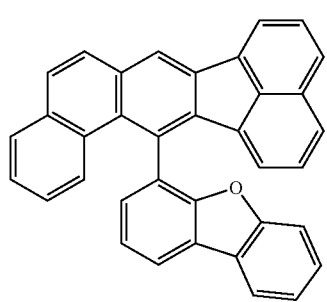
Compound 13
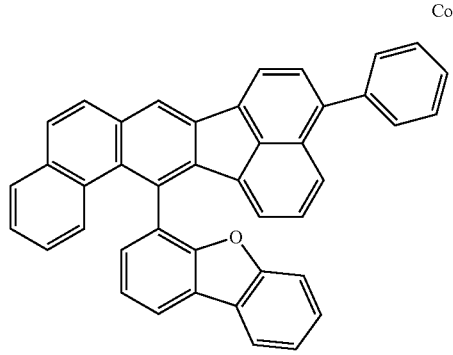
Compound 14
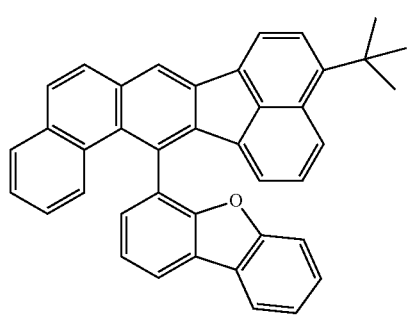
Compound 15
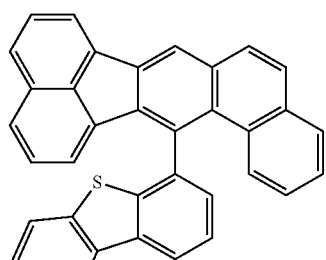
Compound 16
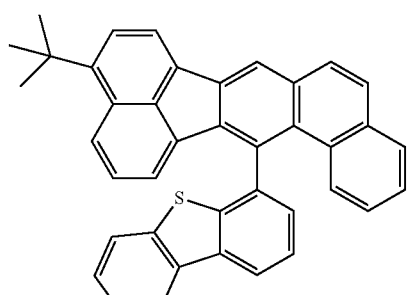
Compound 17
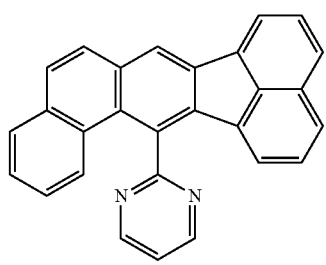
Compound 18
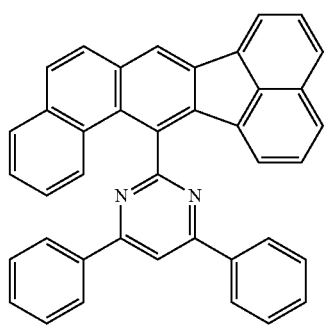
Compound 19
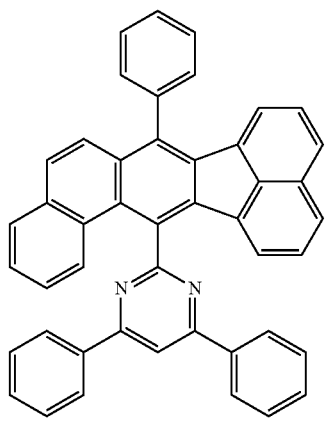

Compound 20

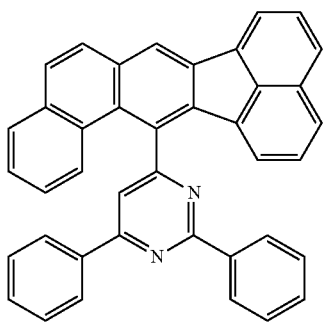

Compound 21

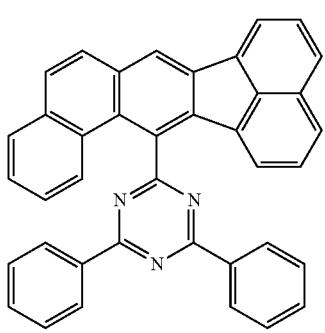

Compound 22

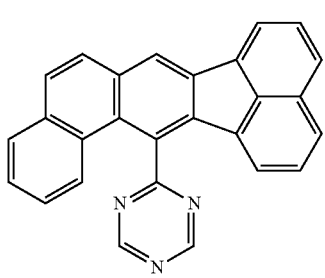

Compound 23

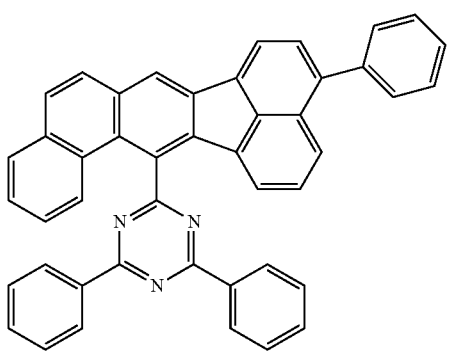

12. An organic light-emitting diode, comprising:
a first electrode;
a second electrode facing the first electrode;
a first emitting material layer between the first and second electrode;
a second emitting material layer between the first electrode and the first emitting material layer or between the first emitting material layer and the second electrode,
wherein the first emitting material layer includes a first host and a first fluorescent dopant,
wherein the second emitting material layer includes a second host and a delayed fluorescent dopant,
wherein the first fluorescent dopant includes an organic compound represented by the following Chemical Formula 1:

Chemical Formula I

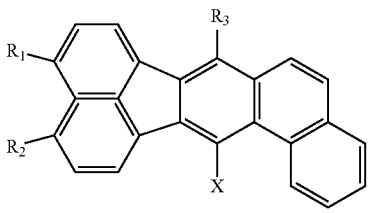

wherein each of $R_1$ to $R_3$ is independently selected from the group consisting of hydrogen, unsubstituted or substituted $C_1$-$C_{10}$ alkyl group, substituted or substituted $C_4$-$C_{30}$ alicyclic group and unsubstituted or substituted $C_5$-$C_{30}$ aromatic group, and wherein X is unsubstituted or substituted $C_4$-$C_{30}$ hetero aromatic group; and wherein an excite singlet energy level of the delayed fluorescent dopant is higher than an excited state singlet energy level of the first fluorescent dopant.

13. The organic light-emitting diode of claim 12, wherein the second emitting material layer is disposed between the first emitting material layer and the second electrode, and further comprising an electron blocking layer between the first electrode and the first emitting material layer.

14. The organic light emitting-diode of claim 13, wherein the first host is formed of a same material as the electron blocking layer.

15. The organic light-emitting material of claim 12, wherein the second emitting material layer is disposed between the first electrode and the first emitting material layer, and further comprising a hole blocking layer between the first emitting material layer and the second electrode.

16. The organic light-emitting diode of claim 15, wherein the first host is formed of a same material as the hole blocking layer.

17. The organic light-emitting diode of claim 12, wherein an excited state singlet energy level of the first host is higher than an excited state singlet energy level of the first fluorescent dopant, and each of an excited state singlet energy level and an excited state triplet energy level of the second host is respectively higher than an excited state singlet energy level and an excited state triplet energy level of the delayed fluorescent dopant.

18. The organic light-emitting diode of claim 12, further comprising a third emitting material layer disposed oppositely to the first emitting material layer with respect to the second emitting material layer, wherein the third emitting material layer includes a third host and a second fluorescent dopant.

19. The organic light-emitting diode of claim 18, wherein the second emitting material layer is disposed between the first emitting material layer and the second electrode, and the third emitting material layer is disposed between the second emitting material layer and the second electrode, and further comprising an electron blocking layer between the first electrode and the first emitting material layer.

20. The organic light-emitting diode of claim 19, wherein the first host is formed of a same material as the electron blocking layer.

21. The organic light-emitting diode of claim 18, wherein the second emitting material layer is disposed between the first emitting material layer and the second electrode, and the third emitting material layer is disposed between the second emitting material layer and the second electrode, and further comprising a hole blocking layer between the third emitting material layer and the second electrode.

22. The organic light-emitting diode of claim 21, wherein the third host is formed of a same material as the hole blocking layer.

23. The organic light-emitting diode of claim 18, wherein an excited state singlet energy level of the delayed fluorescent dopant is higher than an excited state singlet energy level of the first fluorescent dopant and an excited state singlet energy level of the second fluorescent dopant.

24. The organic light-emitting diode of claim 18, wherein an excited state singlet energy level of the first host is higher than an excited state singlet energy level of the first fluorescent dopant, each of an excited state singlet energy level and an excited state singlet energy level and an excited state triplet energy level of the second host is respectively higher than an excited state singlet energy level and an excited state triplet energy level of the delayed fluorescent dopant, and an excited state singlet energy level of the third host is higher than an excited state singlet energy level of the second fluorescent dopant.

25. The organic light-emitting diode of claim 12, wherein X in Chemical Formula 1 is $C_4$-$C_{30}$ hetero aromatic group unsubstituted or substituted with at least one of $C_1$-$C_{10}$ alkyl group and $C_4$-$C_{30}$ aromatic or hetero aromatic group.

26. The organic light-emitting diode of claim 12, wherein the $C_4$-$C_{30}$ hetero aromatic group in Chemical Formula 1 is selected from the group consisting of $C_4$-$C_{30}$ hetero aryl group, $C_4$-$C_{30}$ hetero aralkyl group, $C_4$-$C_{30}$ hetero aryloxyl group and $C_4$-$C_{30}$ hetero aryl amino group, and each of the hetero aryl group, the hetero aralkyl group, the hetero aryloxyl group and the hetero aryl amino group is independently unsubstituted or substituted with at least one of $C_1$-$C_{10}$ alkyl group and $C_4$-$C_{30}$ aromatic or hetero aromatic group.

27. The organic light-emitting diode of claim 12, wherein each of $R_1$ to $R_3$ in Chemical Formula 1 is independently selected from the group consisting of hydrogen, methyl group, tert-butyl group, phenyl group and naphthyl group.

28. The organic light-emitting diode of claim 12, wherein X in Chemical Formula 1 has any one of the following structures:

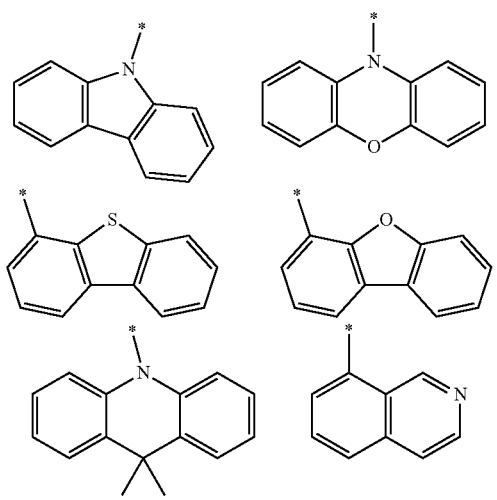

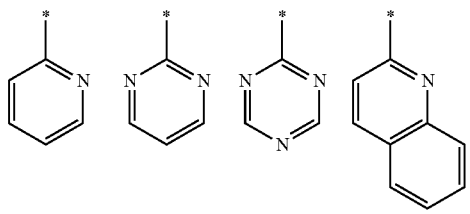

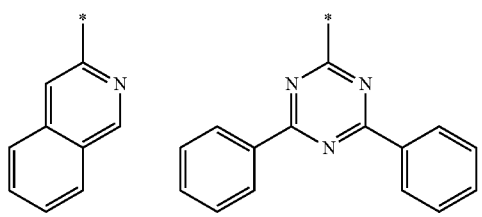

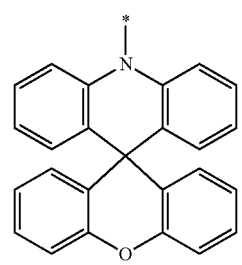

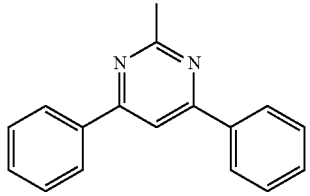

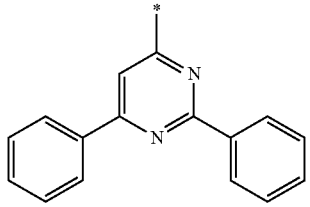 [SMILES: *c1cc(-c2ccccc2)nc(-c2ccccc2)n1]

wherein the asterisk indicates a bonded portion.

29. The organic light-emitting diode of claim 12, wherein the organic compound has one of the following structures of Chemical Formula 2:

Chemical Formula 2

Compound 1

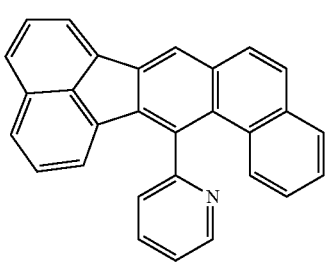

Compound 2
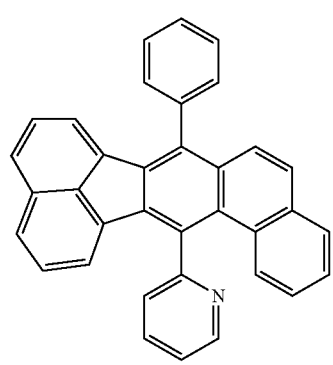
Compound 3
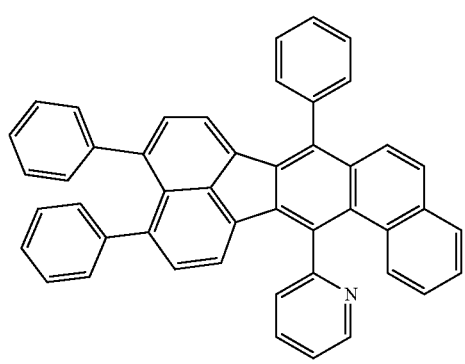
Compound 4
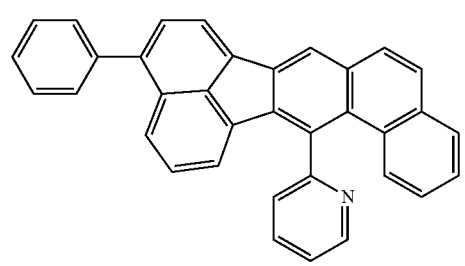
Compound 5
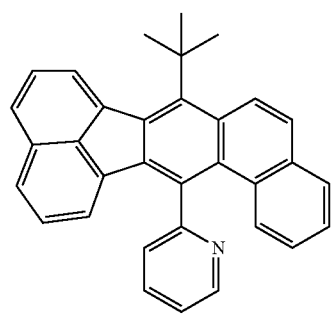
Compound 6
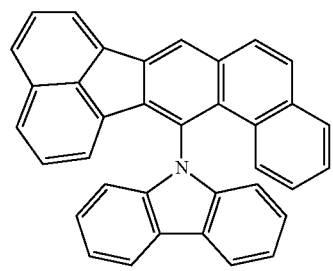
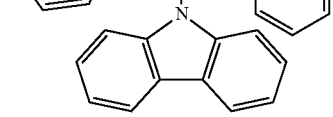
Compound 7
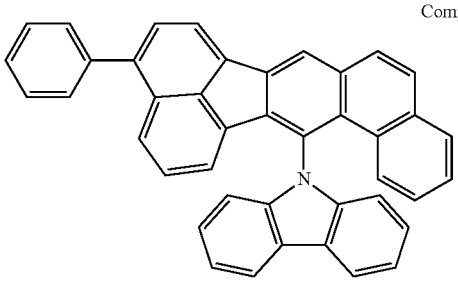
Compound 8
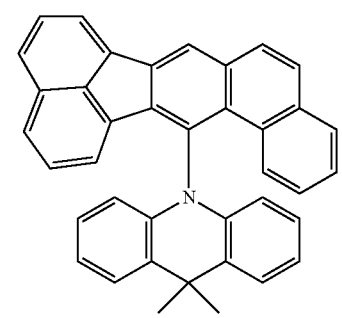
Compound 9
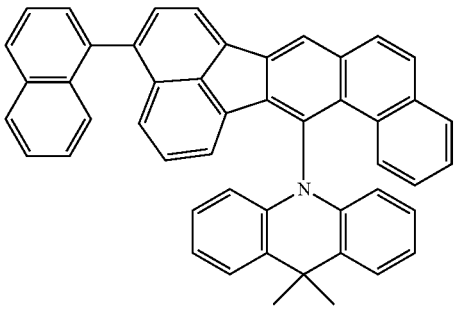
Compound 10
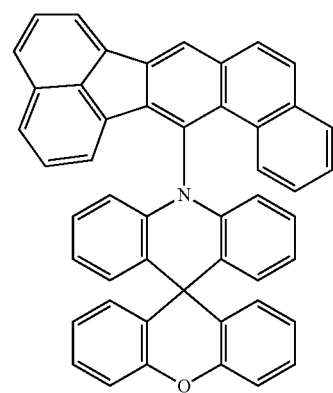

-continued
Compound 11
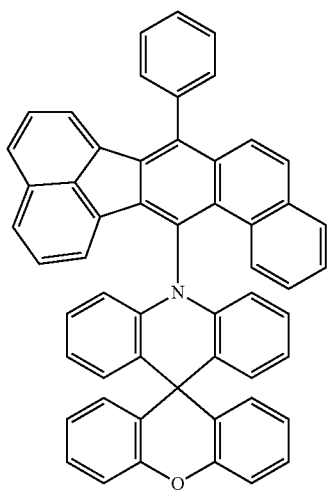
Compound 12
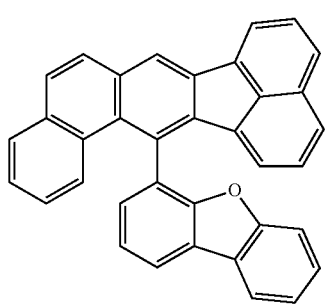
Compound 13
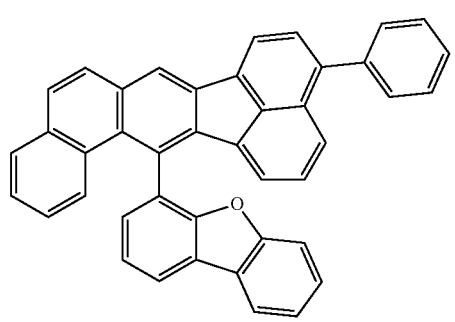
Compound 14
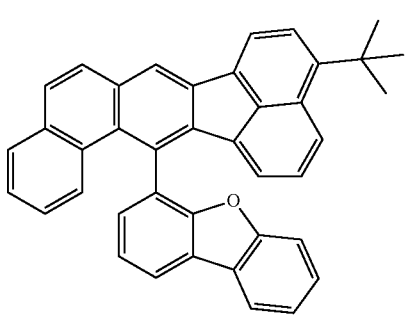
-continued
Compound 15
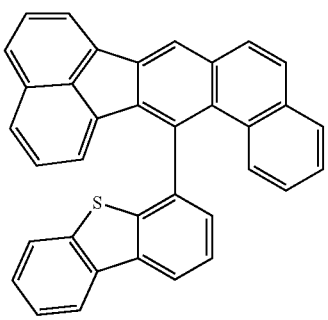
Compound 16
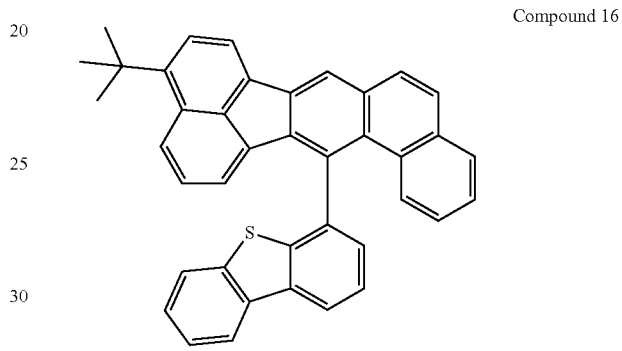
Compound 17
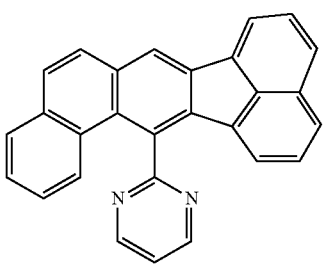
Compound 18
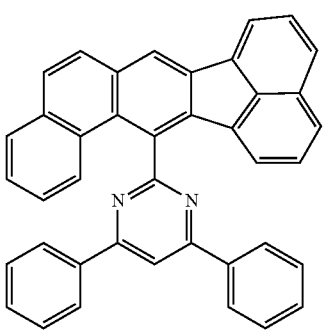

Compound 19
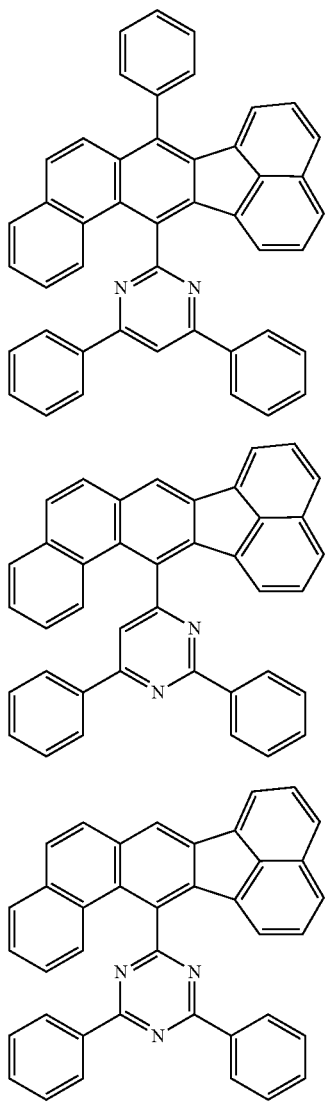
Compound 20
Compound 21
Compound 22
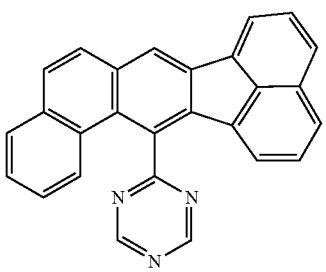
Compound 23
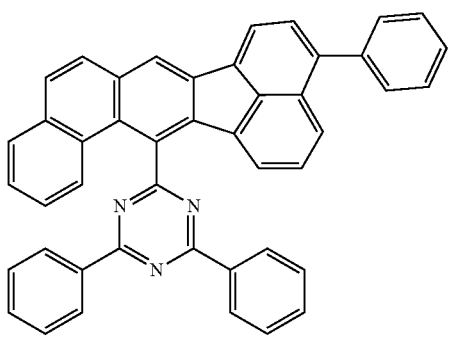
* * * * *